United States Patent
Greenwood

(10) Patent No.: US 8,626,522 B2
(45) Date of Patent: Jan. 7, 2014

(54) CONDITION ANALYSIS

(75) Inventor: Nigel Greenwood, Brisbane (AU)

(73) Assignee: Neurotech Research Pty. Ltd., Queensland (AU)

( * ) Notice: Subject to any disclaimer, the term of this patent is extended or adjusted under 35 U.S.C. 154(b) by 1975 days.

(21) Appl. No.: 10/528,606

(22) PCT Filed: Sep. 19, 2003

(86) PCT No.: PCT/AU03/01232
§ 371 (c)(1),
(2), (4) Date: Nov. 14, 2002

(87) PCT Pub. No.: WO2004/027674
PCT Pub. Date: Apr. 1, 2004

(65) Prior Publication Data
US 2006/0116910 A1    Jun. 1, 2006

Related U.S. Application Data

(60) Provisional application No. 60/412,629, filed on Sep. 20, 2002.

(51) Int. Cl.
G06Q 10/00    (2012.01)
G06Q 50/00    (2012.01)
G06Q 40/00    (2012.01)

(52) U.S. Cl.
USPC ................................ 705/2; 705/3; 705/4

(58) Field of Classification Search
None
See application file for complete search history.

(56) References Cited

U.S. PATENT DOCUMENTS

| | | | |
|---|---|---|---|
| 5,285,793 A * | 2/1994 | Slovut et al. | 600/519 |
| 5,971,922 A * | 10/1999 | Arita et al. | 600/365 |
| 6,381,577 B1 | 4/2002 | Brown | |
| 2001/0013006 A1 | 8/2001 | Brown | |
| 2002/0095099 A1* | 7/2002 | Quyen et al. | 600/544 |

FOREIGN PATENT DOCUMENTS

| WO | WO 94/06088 | | 3/1994 |
|---|---|---|---|
| WO | WO94/06088 | * | 3/1994 |
| WO | WO 03/013351 A1 | | 2/2003 |

OTHER PUBLICATIONS

Friedrich et al, "Extracting Model Equations From Experimental Data" Physics Letters A 271 (2000) 217-222.*
Vincet et al, "Control of a Chaotic System" 1999 University of Arizona pp. 451-465.*
Tuljapurkar et al., "Liapunov Functions: Geometry and Stability", 1979 Journal of Mathematical Biology 8, 25-32.*
Veazie et al., "Treatment Strategies for the Management of Chronic Illness: Is Specialization Always Better?" 2001 System Dynamics Society.*

* cited by examiner

Primary Examiner — Valerie Lubin
Assistant Examiner — Eliza Lam
(74) Attorney, Agent, or Firm — Scully, Scott, Murphy & Presser, P.C.

(57) ABSTRACT

The present invention provides a method of determining a treatment program for a subject. The method includes obtaining subject data representing the subject's condition. The subject data is used together with a model of the condition, to determine system values representing the condition. These system values are then used to determining one or more trajectories representing the progression of the condition in accordance with the model. From this, it is possible to determine a treatment program in accordance with the determined trajectories.

32 Claims, 19 Drawing Sheets

CONDITION ANALYSIS

CROSS-REFERENCE TO RELATED APPLICATIONS

The instant application is a submission under 35 U.S.C. '371 of PCT/AU03/001232 filed on Sep. 19, 2003 and claims the benefit of U.S. provisional patent application 60/412,629 filed Sep. 20, 2002 and Australian Patent Application No. 2002951543 filed on Sep. 20, 2002, the entire contents and disclosures of each of which are incorporated herein by reference.

BACKGROUND OF THE INVENTION

The present invention relates to a method and apparatus for determining a program for a subject, and to a method and apparatus for determining subject parameter values representing the effect of a condition on the subject.

DESCRIPTION OF THE PRIOR ART

The reference to any prior art in this specification is not, and should not be taken as, an acknowledgement or any form of suggestion that the prior art forms part of the common general knowledge.

Currently, it is known to determine medication programs to allow drugs to be administered for different medical conditions. However the determination of the drug programs typically requires years of experimentation. Even then the regimes are typically fairly simplistic and rely on the patient taking specified quantities of medication at various time intervals.

This approach to medication administration suffers from a number of drawbacks. Firstly, the medication regimes are usually general to a condition and not specific to a respective patient. This is important as different patients often respond differently to the same medication regime. Tailored medication regimes are sometimes provided. However, this is currently only possible after monitoring the effect of the empirical medication doses on the patient, which can have a detrimental effect on the patient's health. Furthermore, not all effects of the medication are always readily apparent, so it is not always possible to determine exactly what the effect of the medication has been.

This is exacerbated by the fact that assessment of the effect of medication is usually subjective, and is not quantified to allow the effect of medication to be determined absolutely.

Secondly, it is typical for only a limited number of factors to be taken into account when determining medication regimes. Thus, for example, the researchers will often determine the maximum dose that can be given to a patient without risk, even though in many cases a lower dose provided over a longer time period may be of more benefit.

Finally, it is difficult to predict the effect of the medication in the long term to anything greater than a very general degree, thereby further complicating the possibility of determining medication regimes.

All of these issues are further complicated by the profound non-linearity and complexity in the dynamics of many diseases, including disease progression and adaptation over time.

SUMMARY OF THE PRESENT INVENTION

In a first broad form the present invention provides a method of determining a treatment program for a subject, the method including:

a) Obtaining subject data, the subject data representing the condition;
b) Using the subject data and a model of the condition to determine system values representing the condition;
c) Determining one or more trajectories representing the progression of the condition in accordance with the model and the determined system values; and,
d) Determining a treatment program in accordance with the determined trajectories.

The subject data typically represents the a medical condition for the respective individual, in which case the method includes determining trajectories representing the progression of the medical condition within the individual.

Each system value typically represents a quantity obtained for the measurement of a respective attribute of the condition, the system values including:

a) State variable values representing rapidly changing attributes; and
b) Parameter values representing slowly changing or constant attributes.

The method usually includes determining control variable values, the control variables representing attributes of the condition that can be externally controlled.

The model generally includes one or more model equations representing the condition, the method including determining one or more subject equations in accordance with the model equation(s) and the system values.

The method of determining the treatment program typically includes:

a) Evaluating the behaviour of trajectories representing solutions of the subject equations; and,
b) Determining one or more control programs, each control program including a sequence of control variable values that result in trajectories having desired behaviour.

Typically the method includes determining a set of target points, the target points including stable points for the subject equation(s).

The desired behaviour usually includes at least one of:
a) The trajectories are acceptable;
b) The trajectories do not move away from the target points; and,
c) The trajectories finally approach the target points.

The method generally includes determining the solution trajectories to be acceptable if they are:
a) Non-chaotic; and,
b) Sufficiently smooth.

The method of evaluating the behaviour of the trajectories can include:
a) Determining regions of control variable and/or parameter values for which the trajectories are chaotic; and,
b) Determining ranges of the control variable and/or parameter values for which the trajectories can be made non-chaotic, or otherwise stabilised.

In this case, the method typically including determining one or more control programs in accordance with the determined ranges.

The method can include using a Liapunov function to determine the one or more control programs, although other techniques may also be used.

In the case in which a Liapunov function is used, the method preferably includes:
a) Defining a Liapunov function for which the gradient defines trajectories moving towards the target points;
b) Defining constraints on the control variable values; and,
c) Determining control variable values that result in trajectories travelling down the gradient of the Liapunov function in accordance with the constraints.

The constraints generally include limits on the treatment that can be provided to the subject.

The method typically includes determining a treatment in accordance with one or more of the determined control programs by:
a) Viewing a representation of the trajectories, the representation including an indication of the chaotic regions; and,
b) Selecting a control program in accordance with the represented trajectories.

The method may also further include:
a) Determining one or more Nature values, the Nature values being quantities of Nature parameters and/or variables representing attributes of the condition that will cause the condition to progress in an undesirable manner; and,
b) Modifying the subject equations to incorporate the one or more Nature values;
c) Evaluating the behaviour of modified trajectories representing solutions of the modified subject equations; and,
d) Performing at least one of:
 i) Determining one or more control programs, each control program including control variable values that result in modified trajectories having desired behaviour; and,
 ii) Determining one or more undesired programs, each undesired program including Nature values that result in modified trajectories having undesired behaviour.

Typically, in this case, the Liapunov function is modified to take into account the modified trajectories.

The method generally includes determining a set of undesired points, the undesired behaviour including at least one of:
a) The modified trajectories are unacceptable;
b) The modified trajectories do not move away from the undesired points; and,
c) The modified trajectories finally approach the undesired points.

The method typically includes:
a) Defining a second Liapunov function for which the gradient defines modified trajectories moving towards the undesired points;
b) Defining constraints on the Nature values; and,
c) Determining Nature values that result in modified trajectories travelling down the gradient of the second Liapunov function in accordance with the constraints.

The method usually includes determining the treatment program in accordance with control programs and the Nature programs by:
a) Determining starting points having modified trajectories for which control programs exist;
b) Determining starting points having modified trajectories for which Nature programs exist;
c) Viewing a representation including at least one of:
 i) The modified trajectories;
 ii) The starting points; and,
 iii) The chaotic regions; and,
d) Selecting a control program in accordance with one or more represented trajectories.

The method usually includes determining parameter values by:
a) Determining a partial set of system values from the subject data;
b) Selecting one or more models, each model including a one or more equations representing the effect of a condition on an individual;
c) Attempting to determine a complete set of system values in accordance with the determined partial set of system values and the respective equations; and,
d) Selecting a model in accordance with the determined complete set of system values.

The method of attempting to determine the complete values typically includes:
a) Determining a candidate set of system values in accordance with the determined partial set of system values and the equations; and,
b) Comparing the candidate set of system values to at least one of:
 i) The partial set of system values; and,
 ii) Predetermined thresholds; and,
c) Selecting the model in accordance with the result of the comparison.

The subject is typically a patient, and may be human or non-human. Alternatively, the subject may comprise in vitro samples, such as cells, or the like.

The treatment is typically the administration of medication, but may alternatively, may be the determined modification of any other factor effecting the condition, such as the requirement for the subject to receive predetermined nutrition, exercise, or the like.

In a second broad form the present invention provides apparatus for determining a treatment program for a subject, the apparatus including a processing system adapted to:
a) Obtaining subject data, the subject data representing the condition;
b) Using the subject data and a model of the condition to determine system values representing the condition;
c) Determining one or more trajectories representing the progression of the condition in accordance with the model and the determined system values; and,
d) Determining a treatment program in accordance with the determined trajectories.

In general, the processing system is adapted to perform the method of the first broad form of the invention.

In a third broad form the present invention provides a computer program product for determining a treatment program for a subject, the computer program product including computer executable code which when executed on a suitable processing system causes the processing system to perform the method of the first broad form of the invention.

In a fourth broad form the present invention provides a method of determining system values representing a subject's condition, the method including:
a) Obtaining subject data, the subject data representing the condition;
b) Determining a partial set of system values from the subject data, each system value representing a quantity obtained by the measurement of a respective attribute of the condition;
c) Selecting one or more models, each model including a one or more equations representing the effect of a condition on an individual;
d) Attempting to determine a complete set of system values in accordance with the partial set of system values and the respective equations, for each model; and,
e) Selecting a model in accordance with the determined complete set of system values.

The system values typically include:
a) State variable values representing rapidly changing attributes; and
b) Parameter values representing slowly changing or constant attributes.

The method of attempting to determine the complete values typically includes:
a) Determining a candidate set of system values in accordance with the determined partial set of system values and the equations; and,
b) Comparing the candidate set of system values to at least one of:
   i) The partial set of system values; and,
   ii) Predetermined thresholds; and,
c) Selecting the model in accordance with the result of the comparison.

In a fifth broad form the present invention provides apparatus for determining system values representing a subject's condition, the apparatus including a processing system adapted to:
a) Obtaining subject data, the subject data representing the condition;
b) Determining a partial set of system values from the subject data, each system value representing a quantity obtained by the measurement of a respective attribute of the condition;
c) Selecting one or more models, each model including a one or more equations representing the effect of a condition on an individual;
d) Attempting to determine a complete set of system values in accordance with the partial set of system values and the respective equations, for each model; and,
e) Selecting a model in accordance with the determined complete set of system values.

Typically the apparatus is adapted to perform the method of the fourth broad form of the invention.

In a sixth broad form the present invention provides a computer program product for determining system values representing a subject's condition, the computer program product including computer executable code which when executed on a suitable processing system causes the processing system to perform the method of the fourth broad form of the invention.

In a seventh broad from the present invention provides a method of determining the effectiveness of treatment provided to a subject, the method including:
a) Obtaining subject data, the subject data representing the condition;
b) Using the subject data and a model of the condition to determine system values representing the effect of the condition;
c) Providing treatment to the subject;
d) Repeating steps (a) and (b) to determine modified system values;
e) Comparing the parameter values and the modified system values; and,
f) Determining the effect of the treatment in accordance with the results of the comparison.

The method of determining the system values is preferably a method according to the fourth broad form of the invention.

In an eighth broad form the present invention provides apparatus for determining the effectiveness of treatment provided to a subject, the apparatus including a processing system adapted to:
a) Obtaining subject data, the subject data representing the condition;
b) Using the subject data and a model of the condition to determine system values representing the effect of the condition;
c) Providing treatment to the subject;
d) Repeating steps (a) and (b) to determine modified system values;
e) Comparing the parameter values and the modified system values; and,
f) Determining the effect of the treatment in accordance with the results of the comparison.

Typically the apparatus performs the method of the seventh broad form of the invention.

In a ninth broad form the present invention provides a computer program product for determining the effectiveness of treatment provided to a subject, the computer program product including computer executable code which when executed on a suitable processing system causes the processing system to perform the method of the seventh broad form of the invention.

BRIEF DESCRIPTION OF THE DRAWINGS

An example of the present invention will now be described with reference to the accompanying drawings, in which.

DETAILED DESCRIPTION OF THE PREFERRED EMBODIMENTS

Figure 1:
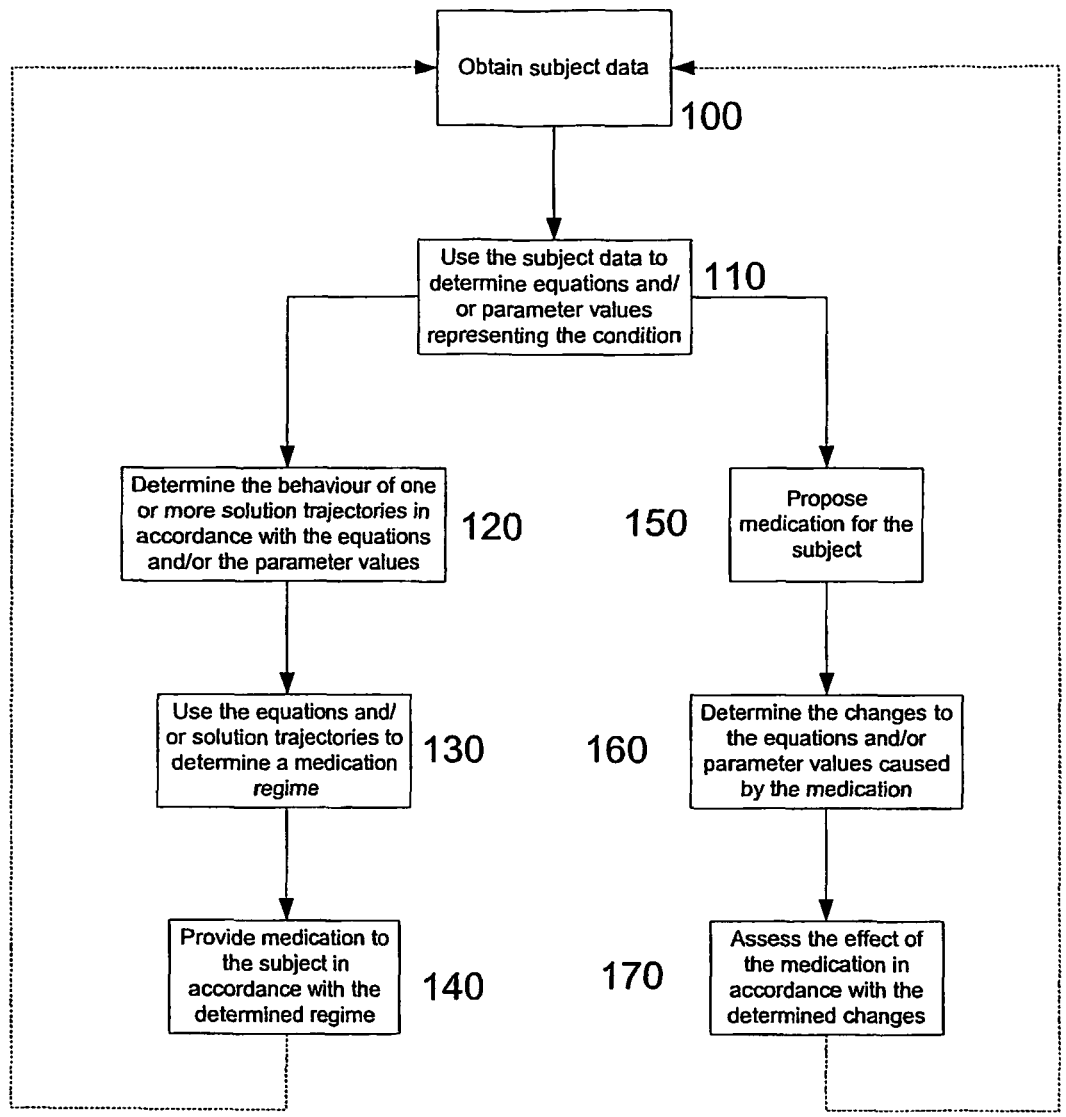
FIG. 1 is a flow chart outlining the process of the present invention.

An overview of the methodology utilised by the present invention to determine a program for a subject having a condition, or to determine parameter values representative of the subject's condition will now be described in outline with reference to FIG. 1.

In particular, whilst the techniques are applicable to any subject, or any condition, the techniques are ideally suited to determining medication programmes for patients having medical conditions, which will now be described in more detail. However, it will be appreciated that the techniques may be extended to any subject, and any condition.

In any event, as shown at step 100 the first stage is for subject data to be obtained.

Typically, the form of the subject data will vary depending on the nature of the subject's condition. Thus, for example, if it is suspected that the subject is suffering from a medical condition such as Parkinson's Disease, the Subject data will typically include information such as MRI brain scans, indications of brain dopamine levels, or the like. However, it will be appreciated that in other conditions, different subject data will be collected. Thus for example, in the case of a condition such as leukaemia, the subject data will typically include an indication of red and white blood cell counts, or the like. Alternatively, the subject may be an athlete, in which case, the condition may be the relative level of fitness for a race, with the subject data relating to indicators of the physical condition of the athlete.

In any event, the subject data is used at 110 to determine equations, variable values, and/or parameter values to represent the condition. In particular, the parameter and/or variable values can be inserted into equations representing the condition to determine one or more equations representing the effects of the condition on the respective subject.

This process can be performed analytically or via numerical analysis of the subject data. Furthermore, aspects of this can be performed manually, although typically as the calculations are complex, a computational aid, such as processing system is used, as will be described in more detail below.

In any event, once the parameter values, variable values and/or equations have been determined at step 110, it is then possible for the behaviour of one or more solution trajectories to be determined in accordance with the equations, variable values and/or the parameter values at step 120. In particular, with the equations effectively modelling the condition of the subject, the solution trajectories generated by solving the equations will represent potential routes of progression of the condition within the individual. Thus, each solution trajectory will effectively model how the condition will potentially develop.

At step 130, the equations and/or the solution trajectories are used to determine a medication or treatment regime. Thus for example, by considering different trajectories that can be followed from the subject's current state, it is possible to select trajectories that may result in an improvement, or at least a reduction in the rate of deterioration of the subject's condition.

The selected solution trajectories are then used to determine a medication or treatment regime. Thus, for example, this may be achieved by determining the level and type of medication that may be provided to the subject to allow one of the selected trajectories which is more beneficial than the others to be followed. Alternatively, this may be used to modify the subjects lifestyle, such as diet and exercise regime, to thereby improve the subject's condition, again in accordance with an appropriate trajectory.

At step 140 it is possible to provide medication to the subject in accordance with the determined regime.

The method can then return to step 100 allowing the process to be repeated. It will be appreciated that this can be performed for a number of reasons.

Firstly, the determined parameter values, variable values, and/or equations may only be accurate over a short duration of time. Thus, as the condition progresses, it may be determined that the condition is no longer following the selected trajectory, for example, if the determined solution trajectory is inaccurate. This may occur for example, because progression of the condition causes an alteration in the model equations such that the solution trajectories determined above are only accurate for the current subject condition. Accordingly, as the condition progresses, new equations, variable values, and/or parameter values, and hence new trajectories may need to be calculated to reflect the new subject condition.

Secondly, new methods of treatment may become available making more advantageous solution trajectories accessible.

Thirdly, it may be determined that the predicted solution trajectories are not being followed, for example indicating that the actual condition of the subject is different to that originally determined.

Fourthly, it may be determined that the original parameter values determined are inaccurate, for example due to errors in the original subject data.

It will be appreciated that other reasons may also exist.

In any event, as the patient's condition progresses, either improving or worsening, it may be necessary to recalculate the parameter values and/or equations to allow revised medication regimes to be produced.

This may also be performed to re-evaluate the parameter values to determine if the selected solution trajectories are being followed or to check if the subject's condition has improved or worsened.

The present invention may also be used in an alternative manner as shown at steps 150 to 170. In this example, the subject's equations, variable values, and/or parameter values are calculated at step 110. Medication and/or treatment is then proposed for and provided to the subject at step 150.

At 160, the changes to the parameter values, variable values, and/or the equations that the provided medication has caused are determined. This allows the effects of the medication and/or treatment to be assessed at step 170.

Accordingly, this can allow drug companies or the like to physically quantify the success of various forms or medication by determining actual parameter values representing the change in the subject's condition after being treated. This helps overcome the usual subjective assessment in which a subject often has to simply indicate whether they feel better after being provided a drug which does not necessary provide the drug company with useful information regarding whether the drug has caused an improvement in the individuals medical condition.

Similarly, in the case of performance animals, this can be used to determine the effect of training and diet to improve their race fitness and health. This is especially useful when dealing with animals in which it is even harder to obtain feedback regarding the animals current state of well being.

A person skilled in the art will appreciate that aspects of the above outlined procedure may be performed manually. However, in order to achieve this it will be necessary for an individual to perform significantly complicated mathematics in order to analyse the subject data, obtain the parameters and/or equations and then determine the medication and/or treatment regime. In particular, some of the calculations generally can only be solved using numerical methods that are beyond the scope of an individual.

Figure 2:
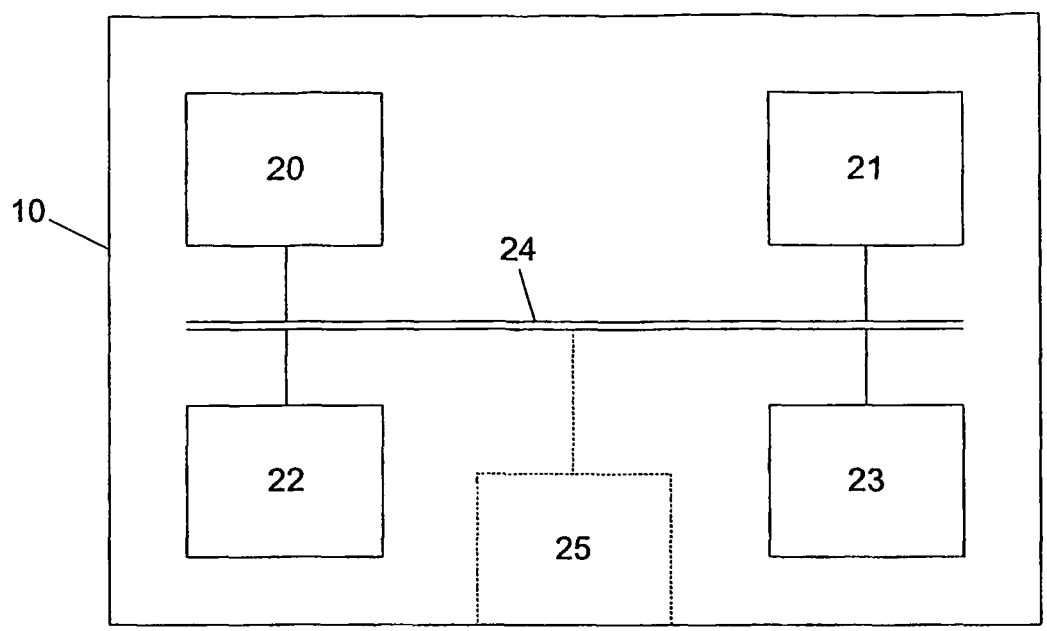
FIG. 2 is a schematic diagram of an example of a system for implementing the present invention.

Accordingly, the invention is typically performed using a processing system that is adapted to receive subject data, and use this to determine either a medication or treatment program, or parameter values that are indicative of the status of a condition. An example of a suitable processing system is shown in FIG. 2.

For the purposes of simplicity, the remainder of the description will focus on the determination of a medication program for a patient, but it will be appreciated that the techniques will equally apply to other forms of treatment and other conditions.

In particular, the processing system 10 generally includes at least a processor 20, a memory 21, and an input device 22, such as a keyboard, an output device 23, such as a display, coupled together via a bus 24 as shown. An optional external interface 25 may also be provided, as will be explained in more detail below.

The subject data is provided to the processing system either via the input device 22 or the external interface 25, and the manner in which this is achieved will depend on the nature of the subject data. Thus for example, in the case of the subject data being an MRI scan, the scan may be supplied directly to the processing system, which is then adapted to analyse the scan to extract the required information. Alternatively, a medical practitioner may be required to evaluate the scan to determine information such as the total brain cell mass therefrom, with this information then being submitted to the processing system.

In any event, once the subject data has been received, the processing system 10 is adapted to execute appropriate applications software stored in the memory 21, to allow the subject data to be analysed to thereby determine the parameter values, variable values, and/or medication program.

Accordingly, it will be appreciated that the processing system may be any form of processing system suitably programmed to perform the analysis, as will be described in more detail below. The processing system may therefore be a suitably programmed computer, laptop, palm computer, or the like. Alternatively, specialised hardware or the like may be used.

In any event, an example of the operation of the processing system 10 in determining a medication regime will now be described in more detail with reference to FIGS. 3 to 6.

In particular, the method of determining a medication regime can be performed at two levels depending on the medical condition and the level of accuracy required.

In the first scenario outlined in FIGS. 3 and 4, it is assumed at first instance that the medical condition is passive. Thus effectively, this assumption indicates that the medical condition will not respond in an unexpected manner to the provision of medication. Thus, it is assumed that if the medication will counteract the effects of the condition, the condition will not then respond to counteract the effects of the medication.

It will be appreciated that this technique is not necessary suitable for all medical conditions but will in any event provide a first level of approximation that can be used in determining a medication regime.

Figure 3A:
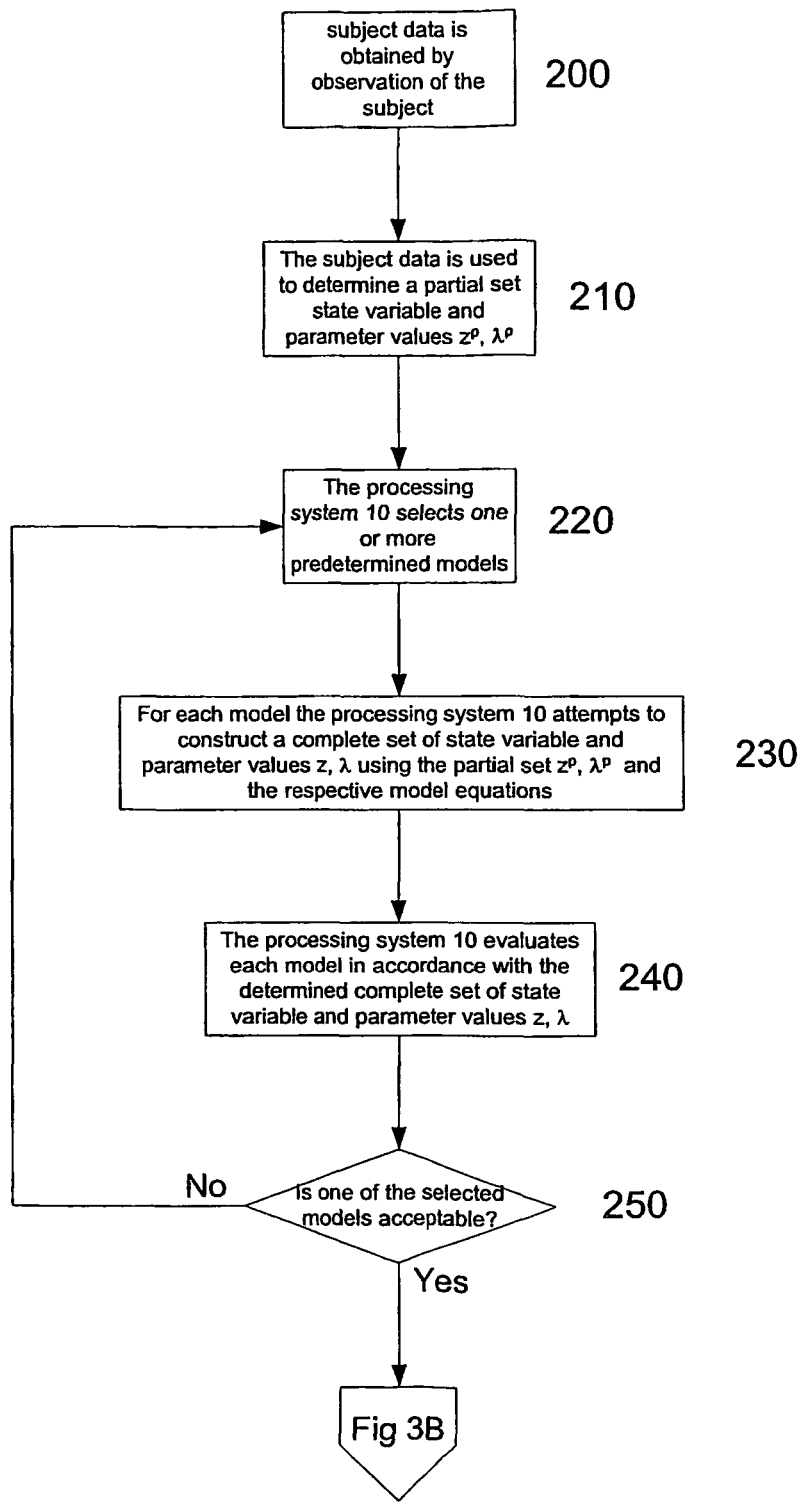
FIGS. 3A and 3B are a flow chart detailing the process of determining a medication program.

In any event, as shown in FIG. 3A the process begins at step 200 when subject data is obtained by observation of the subject. The subject data is then used to determine a partial set of state variable values $z^p$ and parameter values $\lambda^p$, at step 210. The state variable and parameter values $z$, $\lambda$ represent quantities obtained for the measurement of respective attributes of the medical condition, with the partial set $z^p$, $\lambda^p$ being those that can be determined from the subject data.

In particular, the state variable values $z$ are values of measurements that are subject to rapid changes, typically on a day to day scale. Thus, for example, in the case of Parkinson's Disease a state value may reflect the current level of dopamine within the medicated brain, which generally is subject to significant fluctuations on an hour to hour basis.

In contrast, the parameter values $\lambda$ are values of measurements that tend to remain relatively constant on a day to day basis, having only long-term variations. These are therefore slowly changing values that typically will change gradually over a number of months or years. Thus, for example, in the case of Parkinson's Disease, a parameter value may include the number of living dopaminergic brain cells in the individual. It will be appreciated this number of brain cells will typically decay gradually over a few years and is therefore not subject to the rapid change.

It will be appreciated that the partial set of state variable and parameter values $z^p$, $\lambda^p$ may therefore be determined in a number of manners. Thus, for example, the subject data may simply be provided to the processing system 10, which then extracts the partial set of state variable and parameter values. Alternatively however the partial set of state variable and parameter values can be determined manually by a user and then input into the processing system 10.

Furthermore, a database of predetermined state variable and parameter values may be maintained for different medical conditions. The predetermined values may be based on data collected from a number of subjects, and therefore forms generic data regarding the progression of the medical condition in a sample population rather than specific data concerning the progression of the medical condition in a respective individual.

Accordingly, this allows the medical practitioner to select a partial set of state variable and parameter values that correspond to the current level of progression of the medical condition in the individual, which is in turn determined from the subject data. In this case, as the determined values are representative of the medical condition in a general population, any determined medical program will not be specific to the individual, but will be generic to the medical condition.

However, this may provide a sufficiently accurate medication program for many cases. Otherwise, the partial set of state variable and parameter values are determined such that they are specific to the subject, allowing a subject specific medication program to be developed.

In any event, having determined the partial set of state variable and parameter values $z^p$, $\lambda^p$ at step 210, the processing system 10 operates to select one or more predetermined models at step 220.

In general, the processing system 10 will have a number of predetermined models stored in the memory 21. Each of these models will include one or more respective partial and/or ordinary differential equations that represent the progression of a medical condition for a subject.

It will be appreciated that a respective model may be provided for each condition. In addition to this, several different models may be provided for a respective condition. This may be necessary for example if the effect of a condition is different in different individuals, or if the effect of a condition varies depending on the current state of the condition within the subject. Thus, for example, the effect of Parkinson's Disease on an individual will tend to be very different at an early stage, compared to at a later stage when the condition has progressed further. Accordingly, conditions such as Parkinson's Disease will tend to have a significantly different set of ordinary differential equations during initial stages of the condition when compared to the situation in which the condition has progressed significantly within the individual.

Accordingly, the processing system 10 selects one or more of the predetermined models, which on the face of it may model the condition of the subject. Thus for example if the determined condition is Parkinson's Disease, then the processing system 10 can simply select one or more different Parkinson's Disease models.

In order to make the selection, the processing 10 can perform the selection on the basis of input commands provided by a user. Thus for example a trained medical user may provide their own assessment of the condition. Alternatively however the processing system 10 can be adapted to select models in accordance with the partial set of state variable and parameter values $z^p$, $\lambda^p$, provided at step 210.

In any event in steps 230 and 240 the processing system 10 attempts to fit the determined partial set of state variable and parameter values $z^p$, $\lambda^p$ into one of the models.

In order to achieve this at step 230 the processing system 10 attempts to construct a complete set of state variable values z and parameter values $\lambda$ from the partial set of state variable and parameters values $z^p$, $\lambda^p$ and the respective model equations. Thus, the equations will typically specify various relationships between the different state and parameter values, and accordingly, the processing system uses these relationships to determine values for the state variable and parameter values z, $\lambda$ that have not been determined from the subject data.

At step 240, the processing system 10 evaluates each model in accordance with the determined complete set of state variable and parameter values z, $\lambda$.

Thus for example, the processing system 10 will compare the equations for each model to determine whether the determined state variable and parameter values z, $\lambda$ are self consistent, and to determine if these fit with the partial set of state variable and parameter values $z^p$, $\lambda^p$ determined from the subject data.

If it is determined that none of the models are acceptable at step 250 the process returns to step 220 to allow a different model to be selected. Steps 220 to 250 are then repeated until a suitable model is selected.

It will be appreciated that if no suitable model is available, then it may be necessary to determine a new model. This is achieved by performing a numerical analysis of state variable and parameter values for a subject suffering from the medical condition. In particular, variations in the parameter and state variable values over time are determined, and then used to generate partial or ordinary differential equations that best model the changes in the values over time. It will be realised that the developed equations can then be used to predict further changes in parameter values, thereby allowing the differences between predicted and obtained values to be used in improving the model.

In any event, once a suitable model has been accepted at step 250, the process moves on to step 260 to allow the processing system 10 to determine a subject specific model, of the form:

$$dz/dt = f(z, u, \lambda, t) \quad (1)$$

where:
z is a state vector formed from the state variable values such that $z \in \Delta \subset \Re^n$
$\Delta$ is a set of all possible state variable values
u is a control vector formed from control variable values such that $u \in U \subset \Re^p$
U is a set of all possible control variable values
$\lambda$ is a parameter vector formed from the parameter values such that $\lambda \in \Lambda \subset \Re^q$
$\Lambda$ is a set of all possible parameter values
t is time The subject's specific model is obtained by including the state variable and parameter values into the model of equations determined at step 220 to 250 above. In addition to this, the equations will also include a time dependency represented by time t, and a control aspect defined using the control vector u.

The control vector u represents various external factors that can be used to influence the progression of the condition, such as the application of medication, or the like. At this stage, the control vector is generalised and does not include specific values.

Once the equations have been determined, this allows the system equations to be used to generate solution trajectories $\phi$, such that $\phi(z, u, \lambda, t) \subset \Re^n$.

At step 270, the processing system 10 operates to locate reachable equilibrium or other desired points for the subject specific model. The equilibrium points are given by points at which the rate of change of the subject's specific model with respect to time is zero, such that:

$$dz/dt = 0 \quad (2)$$

This is achieved by computing an initial state vector $z^0$ for which $z^0 \in \Delta$, and for which $\exists u^\Psi \in U$, $\lambda^\Psi \in \Lambda$ such that:

$$\lim_{t \to T} \phi(z^0, u^\Psi, \lambda^\Psi, t) \to z^\Psi \in \Delta, \text{ for some } T < \infty \quad (3)$$

where:

$$f(z^\Psi, u^\Psi, \lambda^\Psi, t) \equiv 0, \text{ for all } t > T.$$

Thus, the processing system 10 operates to calculate initial state variable values $z^0$ for which solution trajectories $\phi$ can be steered towards the equilibrium or other desired points as the time t tends towards a sufficiently large value. These solution trajectories $\phi$ represent progressions of the condition that lead to equilibrium or other desired points.

It will be appreciated however that the trajectories $\phi$ may not be trajectories that can be followed in real terms by the subject as they may require excessive levels of drug dosage, or the like. In addition to this, not all of the equilibrium points would represent desirable outcomes for the subject as some of these equilibrium points may correspond to situations in which the condition is significantly worse than at present. Thus, for example, a equilibrium point will typically occur when the subject is dead, which is obviously an undesirable outcome.

Accordingly, at step 280 the next stage is for the processing system to determine those solution trajectories that could potentially be followed by the subjects in real life. In order to do this, the processing system 10 contains a constrained range of control variable values $u^c$ and parameter values $\lambda^c$ for which solution trajectories are acceptable from a particular initial position. Accordingly, this corresponds to determining trajectories emanating from an initial state $z^0$ for which the trajectories can be made acceptable.

In this sense, acceptable solution trajectories are solution trajectories that are non-chaotic and which are sufficiently smooth so that they do not adversely affect the subject. In particular, it is generally not advisable for a subject's condition to be induced to follow a rapidly changing trajectory as this will result in rapid changes in the subject's condition which will generally be detrimental to the subject's overall health.

In order to achieve this, the processing system operates to test for stability as the parameter values $\lambda$ vary.

In particular, the processing system 10 operates to determine parameter values $\lambda$ for which chaos emerges on a subset of all possible state and parameter values, given by:

$$\Lambda^{ch}(\underline{x}) \; \Lambda^{ch} \subset \Lambda(\underline{x}) \Lambda \quad (4)$$

where:
  ⊗ is used to denote the Cartesian product of subspaces

Once a position has been determined for which chaos occurs, the processing system 10 operates to compute eigenvalues $\xi(z, u, \lambda, t)$ and constrained control and parameter values $u^c$, $\lambda^c$ such that the eigenvalues $\xi(z, u^c, \lambda^c, t)$ stabilise the system. This is also used to designate avoidance sets:

$$A = \Delta^A \otimes \Lambda^A \tag{5}$$

where:
  A are the avoidance sets $$\Delta^{ch} \otimes \Lambda^{ch} \subseteq A.$$

Thus, this process allows the extremities of chaotic regions in state space to be determined. This in turn allows the chaotic state space regions to be avoided and/or responded to by the control programs that are subsequently determined, as will be described in more detail below.

In particular, the processing system 10 determines sets $U^c$, $\Lambda^c$ of constrained control and parameter values $u^c$, $\lambda^c$, and uses these sets to determine a region of controllability $R^c \subset \Delta$, in state space. This is performed such that for $z^c \in R^c$, the eigenvalues $\xi(z^c, u^c, l^c, t)$ stabilise the system trajectories $\phi$ into non-chaotic behaviour.

Accordingly, this allows the processing system 10 to determine ranges for the control variable values $u^c$ and parameter values $\lambda^c$ for which the solution trajectories $\phi$ are non chaotic within the state space.

Having determined regions of chaos at step 290, and then used this to determine state space regions where acceptable solution trajectories $\phi$ exist, the processing system 10 operates to determine a family of control programs $p^c$ for which acceptable solution trajectories $\phi$ will be obtained. In particular, the control programs $p^c$ are based on the ranges of the constrained control variable values $u^c$ for which acceptable solution trajectories exist.

Thus, given any initial state vector $z^0 \in R^c$, the control programs $p^c$ can be determined such that the solution trajectories $\phi$ are non-chaotic:

$$p^c(z, \lambda^c, t):R^c \to U^c \tag{6}$$

where:
  $\phi(z^0, p^c(z, \lambda^c, t), \lambda^c, t)$ is non-chaotic.

Having determined a family of control programs $p^c$ this allows a specific control program to be used to determine a medication regime at step 310. This can be performed in a number of different ways.

Thus, for example, the processing system 10 could be adapted to generate all possible solution trajectories $\phi$ that are acceptable and then present these to a user allowing a user to select a solution trajectory $\phi$ which appears appropriate. However, this will typically be computationally very expensive and time consuming and therefore would be undesirable particularly if the system is used on a day to day basis.

Figure 4A:
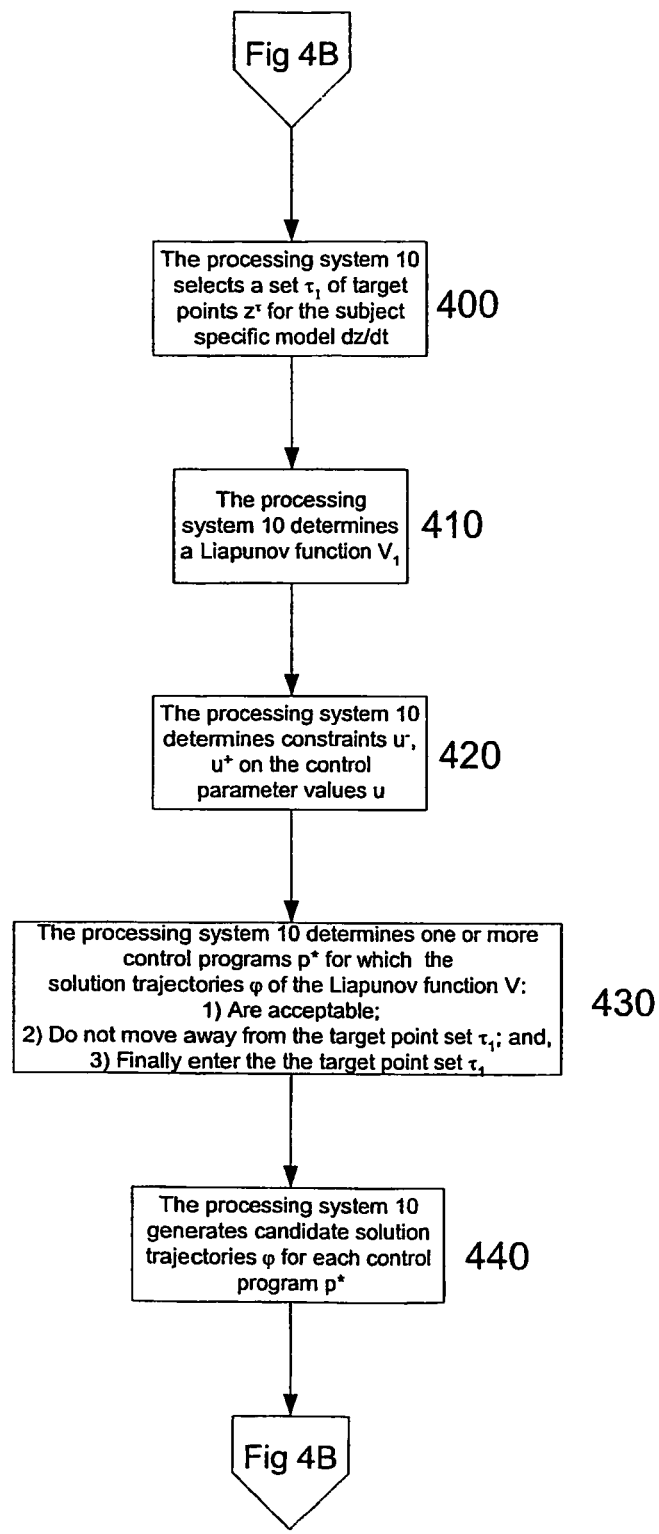
FIGS. 4A and 4B are a flow chart detailing the process of determining the solution trajectories for the method of FIGS. 3A and 3B.
Figure 4B:
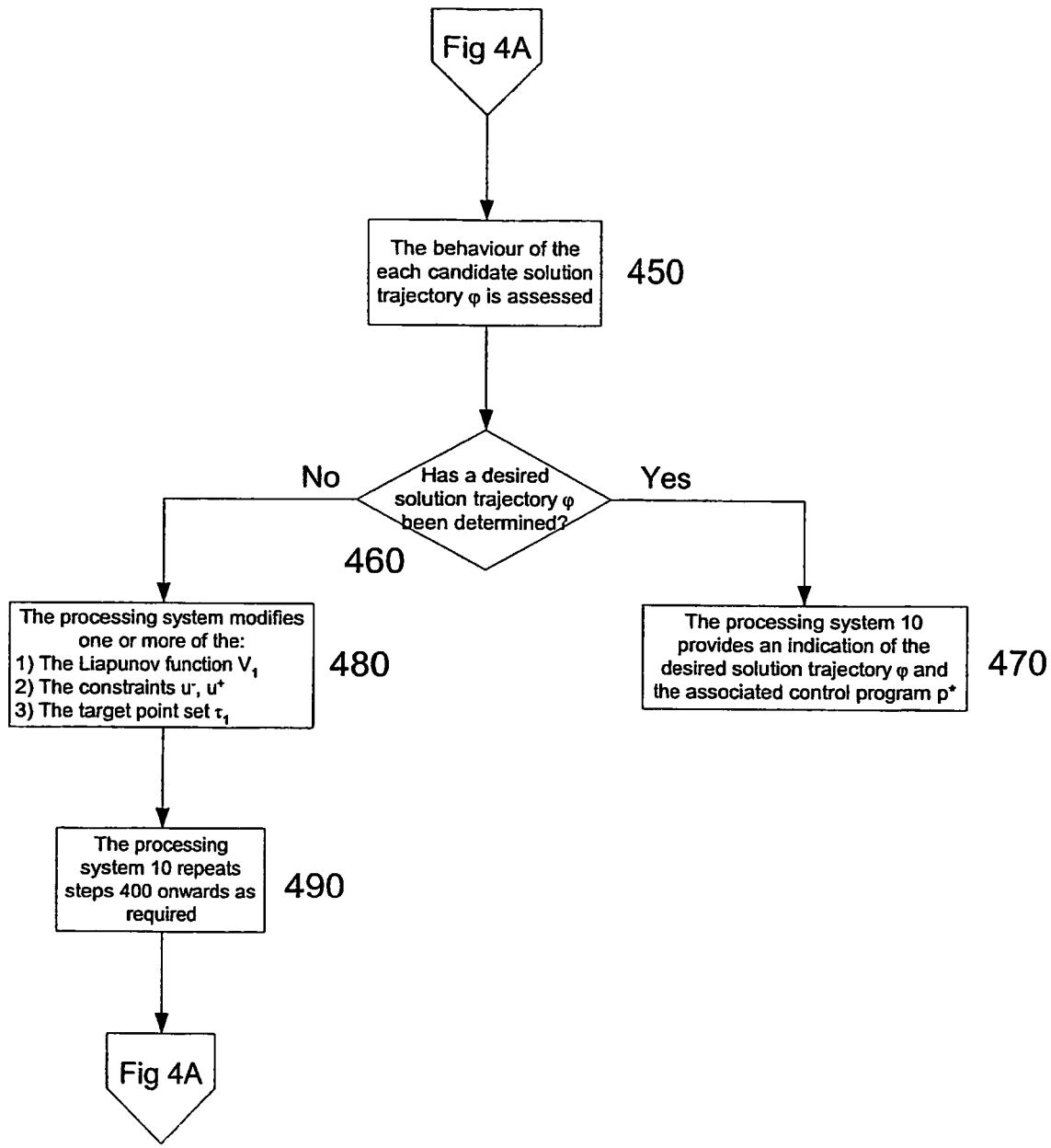

Accordingly, FIGS. 4A to 4B show a particular technique for achieving this using a Liapunov function.

As shown at step 400 in FIG. 4A, this is achieved by having the processing system 10 select a set $\tau_1$ of desirable target points $z^\tau$ for the subject's specific model $dz/dt = f(z, u, \lambda, t)$.

In general, the target points will typically correspond to selected points in the neighbourhood of the equilibrium points determined at step 270 above. Alternatively, points that are otherwise determined to form stable sets may also be used. However, it will be appreciated that this is not the only criteria which would be used to select target points $z^\tau$ and in particular, any equilibrium or stable points corresponding to a deterioration when compared to the subject's current condition will generally be excluded. However, this may not be the case if the subject has a terminal illness for example. In this case, whilst the stable points may be worse than the subject's current condition they may be the best that the subject can hope to achieve.

In any event, the selection of the target points $z^\tau$ may be achieved automatically by the processing system, in accordance with predefined criteria. Alternatively, the target points $z^\tau$ may be selected by a medical practitioner, for example, by evaluating the suitability of the stable points as target points $z^\tau$.

At step 410 the processing system determines a Liapunov function $V_1$. The Liapunov function is based on desired qualitative behaviour to be imposed on system trajectories and it will therefore be appreciated that a number of different Liapunov functions may be selected for any on particular scenario.

It will therefore be something of an art for a user of the system to select the most advantageous Liapunov function, the first time a respective set of equations are solved. However, in general even though the specific equations of the medical condition will vary between subjects it is generally possible for similar equations to use similar Liapunov functions when solution trajectories are being determined. Accordingly, any Liapunov functions used will be stored in the memory 21 so that a database of suitable Liapunov functions is created. Subsequently, Liapunov functions can be selected from the database as required.

In any event, the Liapunov function is determined such that:

$$V_1: \Delta \otimes \Lambda \to \Re, \tag{7}$$

In any event, at step 410 during the creation of the Liapunov function $V_1$ the processing system will operated to define constraints on the parameter values $\lambda$ and the state variable values $z$. These are determined based on the regions of chaos determined at step 280 above.

The safety constraints are determined such that $\lambda \in \Lambda^\tau$, where $\Lambda$ is a bounded set such that $\Lambda^\tau \subset \Lambda$. Thus, this typically involves using a sub-set of the set of constrained parameter values $\Lambda^c$, determined in step 280 above, as will be outlined in more detail below.

Furthermore, a closed set of target points is determined such that:

$$\tau_1 = \{z | V_1(z, \lambda) \leq C_1\} \forall \lambda \in \Lambda^\tau, \tag{8}$$

where:
  $C_1 > 0$, such that $z^\tau \in \tau_1$.

At step 420 the processing system 10 operates to determine constraints on the control variable values u. The constraints are generally defined in accordance with the constrained control variable values $u^c$ determined in step 280 above, although additional constraints may also be applied.

Thus additional constraints $u^-$, $u^+$ may also be defined based on limits on the control of the condition that can be provided to the subject. As control is usually provided in the form of medication, it will be appreciated that the constraints are generally focused on limits for the provision of the medication to the individual. This may be based on factors such as maximum drug dosages, maximum drug dosage rates, maximum drug absorption rates by the body, costs, or the like.

However, in other conditions, other factors may also be influential. This may include for example obtaining regular exercise in the case of high cholesterol levels or heart disease. In this case, restraints will be defined in accordance with exercise regimes proposed for the individual. From this it will be appreciated that whilst medication generally refers to the provision of drugs or other pharmaceutical products to the individual, medication will also generally cover any form of treatments of the condition including for example, dietary requirements, exercise, or the like.

In any event, the constraints are defined such that $u \in [u^-, u^+] \subset U$.

At step 430 the processing system 10 then determines one or more control programs p*, which are effectively control variable values u that are constrained to provide a desired solution trajectories φ. The control programs p* are generated to desired solution trajectories that:

Are acceptable;

Do not move away from the target point set $\tau_1$; and

Finally enter the target point set $\tau_1$.

Thus the at this stage, the processing system 10 effectively operates to exclude solution trajectories that either move away from the target point set $\tau_1$, do not finally enter the target set $\tau_1$, or are not acceptable.

As described in some detail above, acceptable solution trajectories are trajectories that are non-chaotic and are sufficiently smooth. Accordingly, it will be appreciated that the desired solution trajectories will effectively be a sub-set of those trajectories determined to be acceptable at step 280 above.

Thus, the constrained parameter values λ* must at least be a sub-set of the constrained parameter values $\lambda^c \in \Lambda^c$ with the control program p* also being a sub-set of the control variable values, $u^c \in U^c$. This is required to ensure that the desired solution trajectories are acceptable, as well as ensuring that they do not move away from the target point set $\tau_1$ and finally enter the target point set $\tau_1$.

Expressed mathematically, the processing system operates to determine the control program p*:

$$p^*(\lambda^*): \Delta \backslash \tau_1 \to [u-, u+], \quad (9)$$

where:

$\Delta \backslash \tau_1$ denotes the domain of state vectors that fall outside the target set $\tau_1$ λ* are the constrained parameter values determined such that $\lambda^* \in \Lambda^\tau$ and, for all t>0, p*(λ*) attempts to achieve either:

$dV_1/dt<0$ (improvement as the trajectories move closer to the target point set $\tau_1$ with respect to the contours of $V_1$ (z)); or at least, $dV_1/dt=0$ (no worsening as the trajectories do not move away from target point set $\tau_1$ with respect to the contours of $V_1$ (z)).

In any event, once one or more control programs which result in acceptable solution trajectories are determined, the processing system 10 generates candidate solution trajectories φ for each control program p*. This is performed by the processing system 10 at step 440.

In particular, the solution trajectories are determined in accordance with the control program p* and the constrained parameter values λ*. In addition to this, the solution trajectories are determined in accordance with the current state of the subject, which defines an initial state vector $z^0$, such that the solution trajectories are as follows:

$$\phi(z^0, p^*, \lambda^*, t) \quad (10)$$

At step 450 the behaviour of each candidate solution trajectory φ is assessed. This may be achieved in a variety of manners depending on the implementation.

Thus for example, the processing system 10 can be adapted to compare the solution trajectories to predefined criteria. This may include for example comparing end points of each candidate solution trajectory φ to see which end point is closest to a selected one of the target points $z^\tau$, or to determine which solution trajectory end point would be most beneficial for the subject. In addition to this, the processing system may be adapted to determine which candidate solution trajectories φ remain furthest from the chaotic regions at all time, or the like.

Alternatively, the candidate solution trajectories may be assessed by a user of the system.

Figure 5:
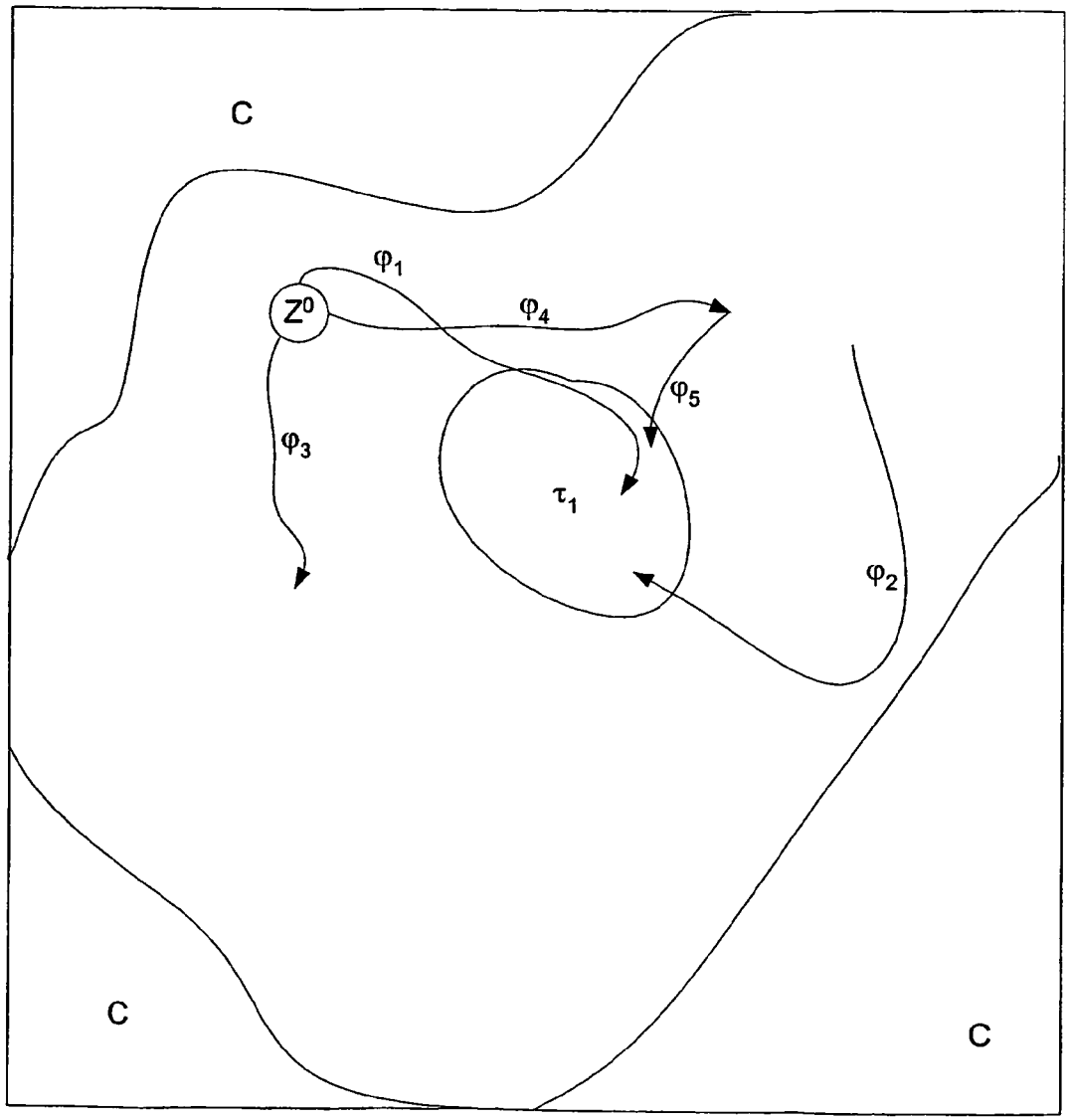
FIG. 5 is an example of a representation generated during the process of FIG. 4B.

In order to achieve this, the processing system 10 can be adapted to generate a representation on the display 23. An example representation is shown in FIG. 5.

As shown, the representation would in general be a two dimensional graphical representation of the state space showing the solution trajectories φ, and regions where solutions to the subject specific equations are chaotic C. The representation could also include examples of the target point set $\tau_1$, and optionally the initial state variable values $z^0$.

This will allow a medical expert to select a solution trajectory that would appear to be most beneficial to the subject. Thus, for example, the trajectory $\phi_1$ leads from the initial start vector $z^0$ to the desired target point set, and would therefore be preferable to other solution trajectories $\phi_2$, $\phi_3$ which do not lead to the desired target point set, or which do not start from the initial start vector $z^0$. However, it will be appreciated that combinations of solution trajectories may also be selected as shown at $\phi_4$, $\phi_5$.

In addition to this it is also possible to select a desired trajectory φ, or modify the control program p* to determine alternative trajectories (p based on either the qualitative behaviour of the trajectories $\phi(z^0, p^*, \lambda^*, t)$ or through quantitative optimisation. This can be achieved for example via analytical methods, such as Euler equations or via adaptive numerical methods, such as through the use of genetic algorithms.

At steps 460 it is determined if a desired solution trajectory φ has been determined. If so, the processing system 10 operates to provide an indication of the desired solution trajectory φ and the associated control program p* at step 470.

This will include a numerically computed solution trajectory $\phi(z^0, p^*, \lambda^*, t)$ and final control program p*, as well as a region of finite controllability $R^q \subset \Delta$ determined such that $\forall z^0 \in R^q, \lim_{t \to T} \phi(z^0, p^*, \lambda^*, t) \to z^\tau \in \tau_1$, for some T>0.

Otherwise the processing system modifies one or more of the Liapunov function $V_1$, the constraints $u^-$, $u^+$ and the target point set $\tau_1$ before repeating steps 400 onwards as required at step 490. This is represented by the link back to 4A as shown.

Again, modification of the constraints and the target points set can be achieved in a number of ways, such as via analytical or adaptive numerical methods. Alternatively, this can be achieved manually via consideration of the constraints and the target points set.

Thus, for example, a medical practitioner can consider the constraints determined based on the treatment, such as the medication available, and consider whether this can be adapted. Thus for example, can alternative drugs, or higher doses be used. Similarly, if the desired target points $\tau_1$ cannot be reached, can other slightly less desirable target points be reached.

As described above, this example relies on the condition being passive. However, in many case, the condition is not passive and instead responds to medication or the like, to attempt to counteract the effects of the medication. Thus, for example, if medication is provided to a subject, the subjects condition may fight against the action of the medication by altering it's behaviour patterns in an attempt to counteract the effects the medication. Thus, for example, in the case of immune deficiency conditions, the provision of drugs to kill a virus may result in an initial increase in viral levels as the virus reproduces in an attempt to counteract the effect of the drugs.

Alternatively, steps 260-460 may have revealed that the system behaviour depends on some state variable or parameter value, which is measurable only up to a margin or certainty. The worst case scenario inherent in this margin of uncertainty must be assessed now.

In order to account for this, a modified method can be used which is classed as a "Game against Nature" type problem.

Again, this form of problem can be dealt with in a number of ways. However, a specific example will now be described with reference to FIGS. 6 to 8 in which Nature values w are used to represent the action of the condition to counteract the effects of any medication. This may be achieved by using a Nature vector w formed from Nature parameter values such that $w \in \Xi \subset \Re^m$.

In particular, "Nature" is taken to be a sentient opponent that calculates the best possible choice of values for opposing the efforts of the clinician within the determined constraints. Accordingly, the Nature vector w will be designed to take into account factors such as system noise uncertainty, instrument uncertainty, drug administration noise and condition progression as well as other possible sources of uncertainty or pathology.

The Nature values are therefore quantities of Nature parameters and/or Nature variables representing attributes of the medical condition that will cause the medical condition to progress in an undesirable manner. Thus, it will be appreciated that the Nature parameters are slowly changing attributes, with the Nature variables being rapidly changing attributes.

Accordingly, at step 500, the processing system determines various Nature parameter and/or variable values.

The specific Nature values may be determined by a medical user, or the like, in accordance with observations of the subject and/or condition. Alternatively, Nature values may be selected from predetermined Nature values determined for specific conditions.

At step 510, the processing system 10 utilises the Nature values w to determine a modified subject specific model:

$$dz/dt = f(z, u, w, \lambda, t) \quad (11)$$

Again these system equations generate solution trajectories $\phi(z^0, u, w, \lambda, t) \subset \Re^n$.

As in the previous example, the processing system 10 operates to locate equilibria and qualitative system behaviour for the subject's specific model dz/dt, at step 520.

The processing system 10 then determines a range of control variable values $u^{cw}$ and parameter values $\lambda^{cw}$ for which solution trajectories $\phi$ are acceptable.

Again, this will involve testing the solution trajectories $\phi$ to find regions of chaotic behaviour in state space, in a manner similar to that described above with respect to FIG. 3B. The processing system 10 will then compute eigenvalues $\xi$ (z, u, w, $\lambda$, t), and control variable and parameter vectors $u^{cw}$, $\lambda^{cw}$ such that $\xi$ (z, $u^{cw}$, w, $\lambda^{cw}$, t) stabilises the system for $\forall w \in \Xi$. The processing system 10 uses these values to determine the avoidance sets $A^{ch}$ such that $\Delta^{ch}(x) \Lambda^{ch} \subset A^{ch}$.

Having determined state space regions for which acceptable solution trajectories exist despite the effects of the Nature vector w, at step 540, the processing system moves on to step 550 to determine a family of control programs $p^{cw}$ in accordance with the determined ranges of control variable values $u^{cw}$ and parameter values $\lambda^{cw}$.

In particular, the processing system 10 computes a region of controllability $R^{cw}$ in state space, such that given any initial state vector $z^0 \in R^{cw}$, the control programs $p^{cw}$ are based on the control variable values $u^{cw}(z^0, w, \lambda^{cw}, t)$ such that solution trajectories $\phi(z^0, u^{cw}(z^0, w, \lambda^{cw}, t) w, \lambda^{cw}, t)$ are non-chaotic for $\forall w \in \Xi$, despite the effects of the Nature vector w.

At step 560, the family of selected control programs $p^{cw}$ is used to determine a medication regime.

Figure 6:
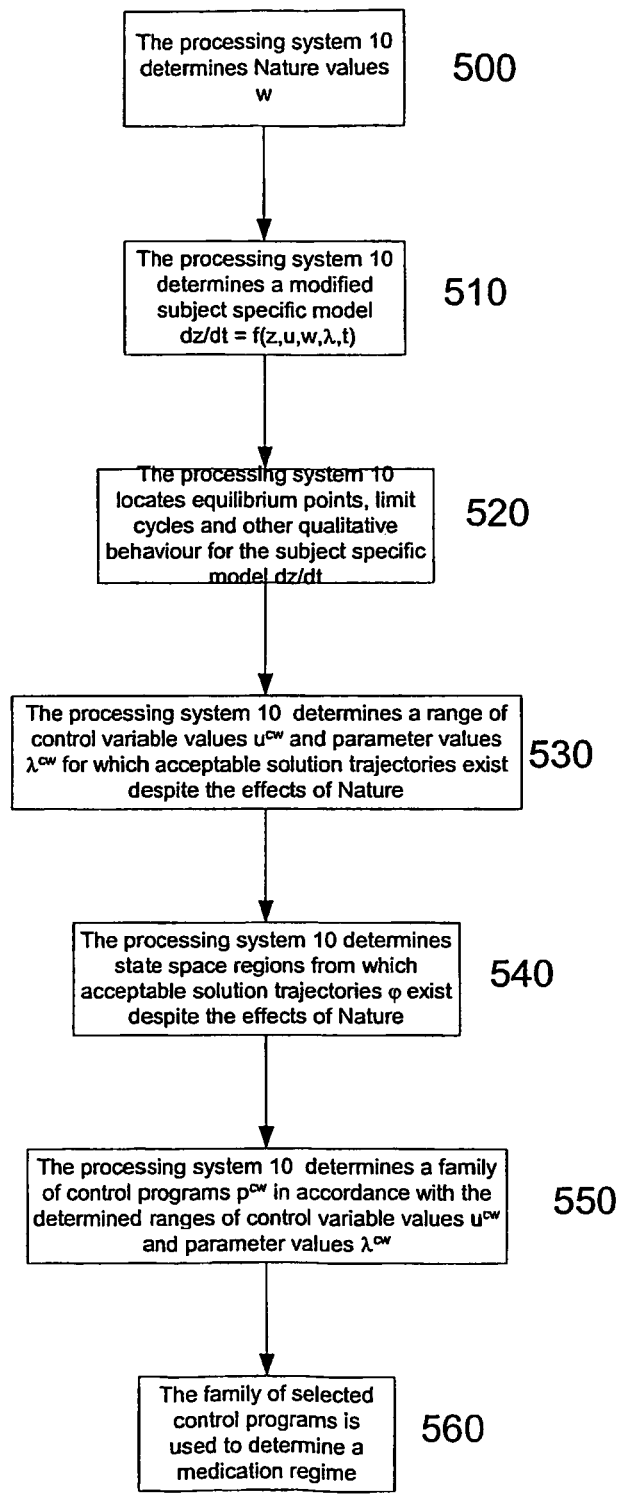
FIG. 6 is a flow chart detailing the process of determining a medication program including accounting for Nature values.

Again, the procedures set out in FIG. 6 may be performed in a number of manners. However, in this example, the processing system determines a second Liapunov function that is used to represent the effects of Nature, such as the effects of the medical condition and other noise or uncertainty factors.

Figure 7A:
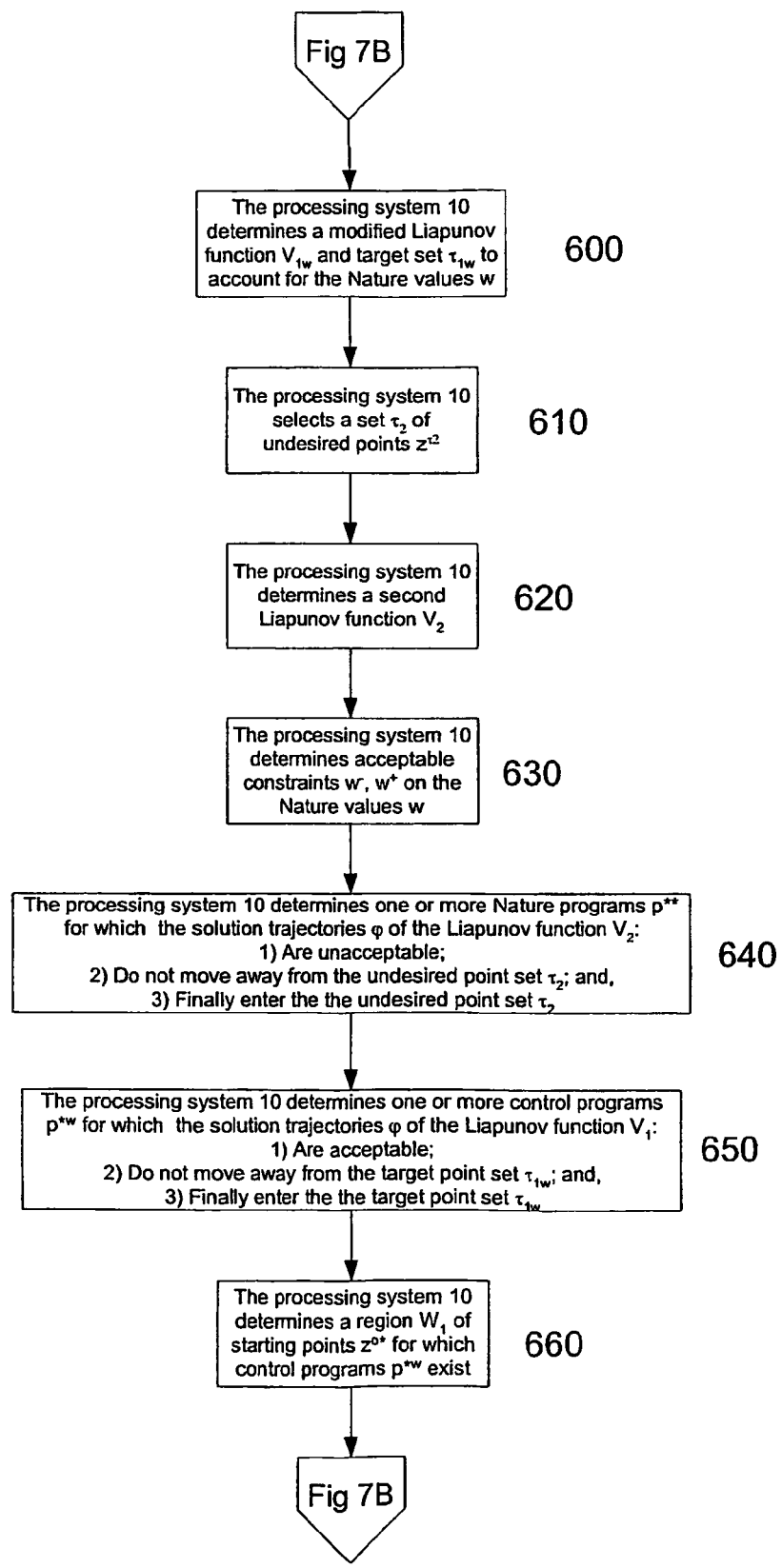
FIGS. 7A and 7B are a flow chart detailing the process of determining the solution trajectories for the method of FIG. 6.
Figure 7B:
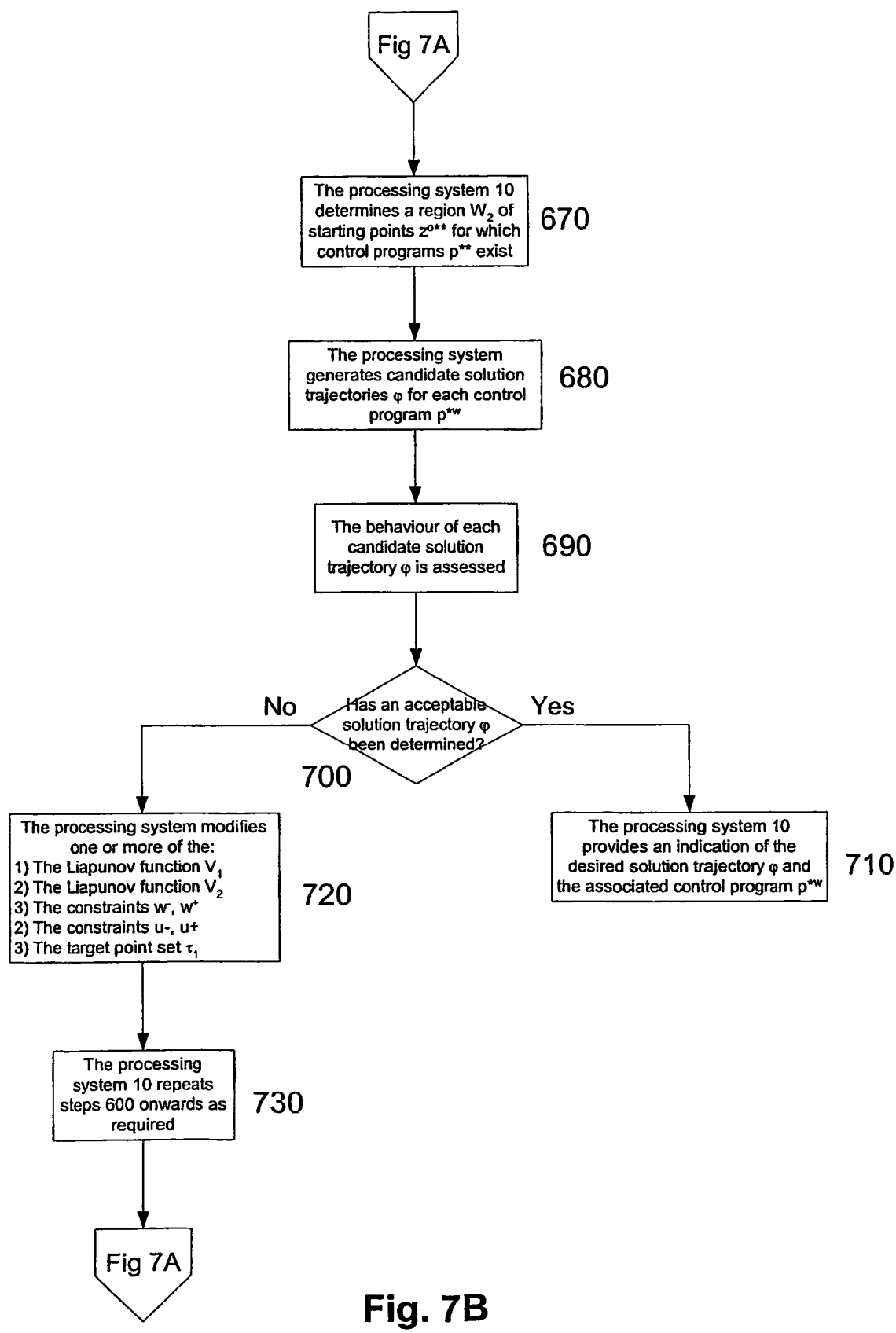

Thus, as shown in FIG. 7A, at step 600 the processing system 10 determines a modified first Liapunov function $V_{1w}$ and corresponding target point set $\tau_{1w}$. In this case, the Liapunov function $V_{1w}$ is a modified version of Liapunov function $V_1$ used in FIGS. 4A and 4B, which has been modified to take into account the Nature values w.

Once this has been completed, the processing system 10 then operates to select a set $\tau_2$ of undesired points $z^{\tau_2}$ at step 610. These undesired points $z^{\tau_2}$ will correspond to lethal or extremely undesired points which maybe detrimental to the health of the subject if the subject's condition were to pass through these locations.

The set of undesired points $\tau_2$ can be determined based on:

$$\tau_2 = \{z | V_2(z, \lambda) \leq C_2\}, \quad (12)$$

$$A^{ch} \subseteq \tau_2(x) \Lambda^{\tau_2} \quad (13)$$

where:

$C_2 > 0$ $\Lambda^{\tau_2} \subseteq \Lambda$

This allows the processing system 10 to define a large avoidance set $A = \Delta^A(x) \Lambda^A$ such that $\Lambda^{\tau_2} \subseteq \Lambda^A \subseteq \Lambda$, $\tau_2 \subseteq \Delta^A \subset \Delta$.

At step 620, the processing system 10 determines a second Liapunov function $V_2$. The purpose of this second Liapunov function $V_2$ is to model the operation of the Nature values w as a hostile entity, to thereby embody "enemy" behaviour of noise/uncertainty and condition progression. Accordingly, the second Liapunov function $V_2$ determines solution trajectories representing the progression of the medical condition under the influence of the Nature vector, which causes a worsening in the medical condition, as far as controlling or preserving the subject's health is concerned. These solution trajectories will hereinafter be referred to as undesirable trajectories.

The second Liapunov function is defined such that $V_2$ : $\Delta(x) \Lambda \rightarrow \Re$.

At step 630, the processing system 10 determines acceptable constraints on the Nature values w.

As described above, the Nature values w are determined on the basis of factors such as the system noise, instrument uncertainty, drug administration noise, or the like. Accordingly, a number of these values will be determined based on the manner in which subject data was obtained, the method of drug delivery, inaccuracies in drug administration methods and the like.

This can be used to determine the areas that introduce the most uncertainty or lack of confidence into determining and treating the subject's condition. Thus, for example, if it is determined that there is a high level of confidence associated with existing tolerances in measurements of ligand, it will be appreciated that massive investment into obtaining more accurate measurement tolerances would be relatively worthless.

Accordingly, assessing the Nature values in itself is useful, as it will allow areas of low control confidence to be identified, allowing these issues to be addressed in preference to other issues which introduce less threat.

It any event, at step 640, the processing system 10 determines one or more Nature programs p which cause the undesirable trajectories acting under the influence of the Liapunov functions $V_2$ to move towards the set of undesired points $\tau_2$. This is performed at step 640 to allow the processing system 10** to determine the worst effects of changes in the medical condition. Thus, this effectively represents the circumstances in which the medical condition deteriorates or an uncertainty presents itself in the worst possible fashion, as far as controlling or preserving the subject's health is concerned.

In particular, for a given initial state vector $z^0 \epsilon \Delta \backslash (\tau_2 \cup \Delta^A)$ the processing system operates to determine a Nature program p** given by:

$$p^{**}:\Delta\backslash(\tau_1 \cup \Delta^A) \rightarrow [w^-, w^+] \quad (14)$$

where:

$\Delta^A$ is the avoidance set such that $\tau_2 \subseteq \Delta^A$ and, for all t>0, p** attempts to achieve either:

$dV_2/dt<0$ (deterioration as undesirable trajectories move closer to the undesired point set $\tau_2$ with respect to the contours of $V_2$ (z)); or at least, $dV_2/dt=0$ (no improvement as undesirable trajectories do not move away from the undesired point set $\tau_2$ with respect to the contours of $V_2$ (z)).

Accordingly, the family of Nature programs p** represents the set of the condition's strongest "choices" of control strategy to resist therapy.

At step 650 the processing system 10 operates to determine one or more control programs p*w for which the solution trajectories are acceptable and do not move away from the target point set $\tau_{1w}$. Thus, this corresponds to finding solution trajectories representing the progression of the condition in which the solution trajectories are non-chaotic and smooth, and after which the progression does not worsen, despite the best efforts of Nature.

In particular, for a given initial state vector $z^{0*} \epsilon \Delta \backslash (\tau_{1w} \cup \Delta^A)$ the processing system operates to determine a control program p*w such that:

$$p^{*w}:\Delta\backslash(\tau_{1w} \cup \Delta^A) \rightarrow [u^-, u^+] \quad (15)$$

such that:

$$\lim_{t \to T} \phi(z^0, p^{*w}, w, \lambda, t) \rightarrow z^\tau \epsilon \tau_{1w}; \text{ for } T>0; \quad (16)$$

$$\forall \lambda \epsilon \Lambda^{\tau_{1w}}$$

$$\forall w \epsilon [w^-, w^+];$$

where:

$\Delta^A$ is the avoidance set, such that $\tau_2 \leq \Delta^A$ and, for all t>0, p*w attempts to achieve either:

$dV_{1w}/dt<0$ (improvement as trajectories move closer to the target point set $\tau_{1w}$ with respect to the contours of $V_{1w}$ (z)); or at least, $dV_{1w}/dt=0$ (no worsening as trajectories do not move away from the target point set $\tau_{1w}$ with respect to the contours of $V_{1w}(z)$)

Thus, the processing system 10 effectively determines initial state functions for which a control program can be determined that steers the solution trajectories towards the desired target point set $\tau_{1w}$ despite the best efforts of the disease to achieve deterioration or stalemate. The control program p*w therefore represents the clinicians' "strongly-winning strategy", with the family of such control programs p*w representing the set of the clinicians' strongest choices of control strategy to achieve the desired target point set $\tau_{1w}$.

Accordingly, from this it will be appreciated that the processing system 10 determines one or more Nature programs p** and one or more control programs p*w which represent the strongest control strategy for the condition and the strongest control strategy for the clinician respectively.

At step 660 the processing system 10 operates to determine a region $W_1$ of initial state variable values $z^{0*}$ for which control programs p*w exist. Thus effectively, the processing system 10 operates to examine the solution trajectories and determine values for the control, parameter and Nature values for which control programs p*w exist.

Thus, the processing system 10 operates to determine:

$$W_1 = \{z^{0*} \epsilon \Delta \backslash (\tau_{1w} \cup \Delta^A) \text{ such that } p^{*w} \text{ exists.}\} \quad (17)$$

At step 670 the processing system 10 operates to similarly determine regions $W_2$ of initial state vectors $z^{0}$ for which Nature programs p exist.

Thus effectively, the processing 10 works out initial state vectors $z^{0}$ which result in undesirable trajectories that follow the Nature programs p and state vectors $z^{0*}$ for which the solution trajectories follow the control programs p*w.

The processing system then generates candidate solution and undesirable trajectories for each control program p*w, and each Nature program p at step 680**.

The behaviour of each candidate trajectory is then assessed at step 690.

Again, this may be achieved in a number of ways and may be achieved for example automatically by having the processing system analyse the candidate trajectories and choose the solution trajectories that will most benefit the subject.

Figure 8:
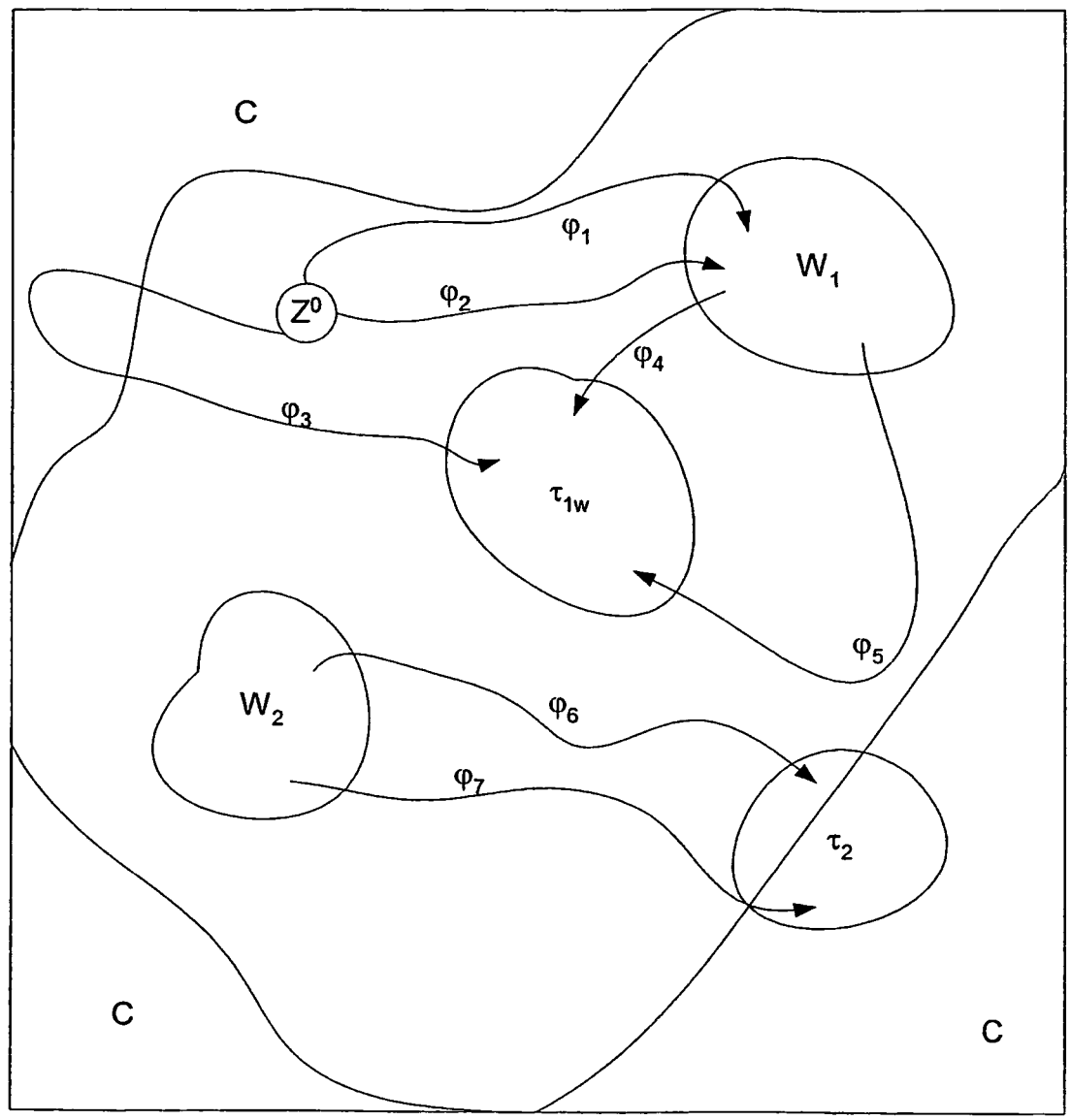
FIG. 8 is an example of a representation generated during the process of FIG. 7B.

However, typically this is achieved by having a professional medical staff member examine a representation showing the regions $W_1$, $W_2$, the chaotic regions C and the solution trajectories $\phi$ as shown in FIG. 8.

Thus as shown, regions of chaotic behaviour as shown at C, with the regions of undesired point set $\tau_2$ and target point set $\tau_{1w}$ and initial regions $W_1$, $W_2$ as shown.

In use, the medical practitioner would determine the subject's initial state variable values that form the state vector $z^0$. The medical practitioner then selects one or more trajectories from this point that will ultimately allow the subject's medical condition to move towards the target point set $\tau_{1w}$.

In this example, seven different trajectories are shown as $\phi_1$ to $\phi_7$ respectively.

In this example only a single one of the trajectories $\phi_3$ extends from the initial starting point $z^0$ to the target point set $\tau_{1w}$. However, this trajectory $\phi_3$ enters a chaotic region C that can therefore instantly be dismissed.

The trajectories $\phi_6$ and $\phi_7$ ultimately end at the undesired point set $\tau_2$ and again, it would be undesirable to follow or even approach these trajectories.

Accordingly, it will be necessary for the subject regime to cause a subject to progress along one of the trajectories $\phi_1$, $\phi_2$ to the region $W_1$ and then follow one of the trajectories $\phi$, $\phi_5$ to the target point set $\tau_{1w}$. In this example the trajectories $\phi_1$, $\phi_5$ both near regions of chaos C and accordingly, the trajectories $\phi_2$, $\phi_4$ would be selected.

Once an acceptable trajectory is determined at step 700 the processing system 10 provides an indication of the desired solution trajectory and the associated control programs p*w. It will be appreciated that in this example, two solution trajectories are required and accordingly two corresponding control programs p*w will be required. In this instance, the first control program will cause the subject's condition to progress along the trajectory $\phi_2$ with the second control program causing the subject trajectory condition to move along the trajectory $\phi_4$ thereby ending within the target point set $\tau_{1w}$.

In the event that a suitable solution trajectory has not been determined then the processing system moves on to step 720 to modify one or more of the Liapunov function $V_1$, the Liapunov function $V_2$, the Nature parameter constraints $w^-$, $w^+$, the control parameter constraints $u^-$, $u^+$ and the target point set $\tau_{1w}$.

The processing system 10 then repeats step 600 onwards as required.

Architectures

It will be appreciated that the above method may be achieved in a number of different manners. Thus, for example, a respective processing system 10 may be provided for each medical practitioner that is to use the system. This could be achieved by supplying respective applications software for a medical practitioner's computer system, or the like, for example on a transportable media, or via download. In this case, if additional models are required, these could be made available through program updates or the like, which again may be made available in a number of manners.

However, alternative architectures, such as distributed architectures, or the like, may also be implemented.

Figure 9:
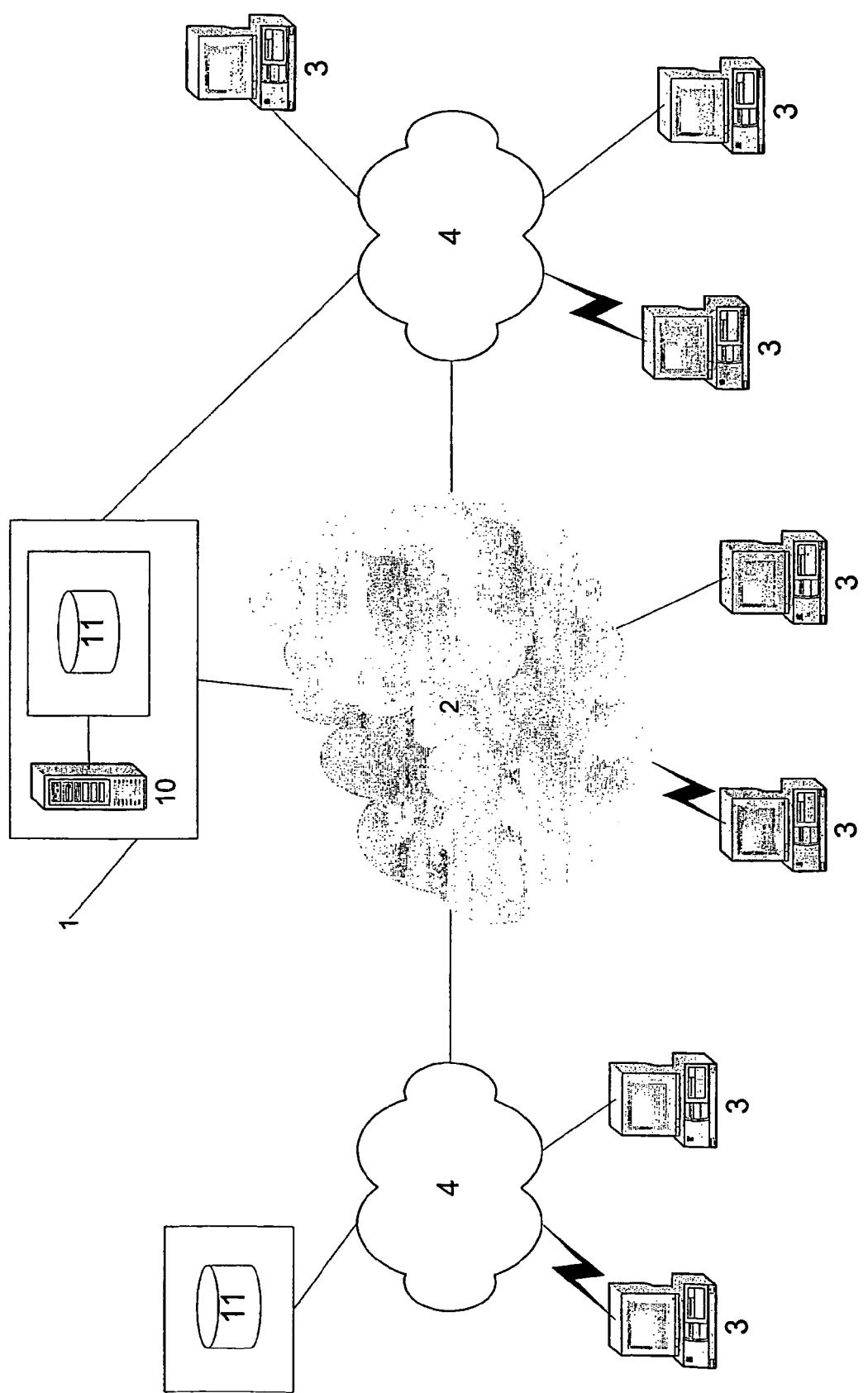
FIG. 9 is a schematic diagram is an alternative example of a system for implementing the invention.

An example of this is shown in FIG. 9 in which the processing system 10 is coupled to a database 11, provided at a base station 1. The base station 1 is coupled to a number of end stations 3 via a communications network 2, such as the Internet, and/or via communications networks 4, such as local area networks (LANs) 4. Thus it will be appreciated that the LANs 4 may form an internal network at a doctor's surgery, hospital, or other medical institution. This allows the medical practitioners to be situated at locations remote to the central base station 1.

Accordingly, in use the end stations 3 must be adapted to communicate with the processing system 10 positioned at the base station 1. It will be appreciated that this allows a number of different forms of end station 3 may be used.

Figure 10:
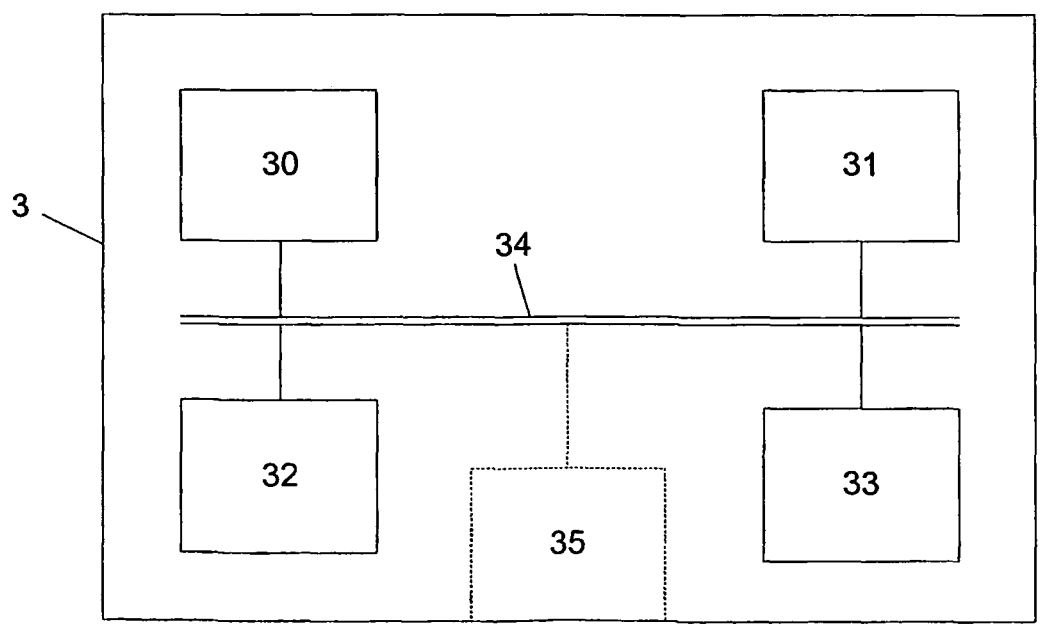
FIG. 10 is a schematic diagram of one of the end stations of FIG. 9.

An example of a suitable end station is shown in FIG. 10. As shown the end station 3 includes a processor 30, a memory 31 and an input device 32 such as a keyboard, an output device 33 such as a display coupled together via a bus 34, as shown. An internal interface 35 is typically provided to allow the end station to be coupled to one of the communications networks 2, 4.

In use, the processor 30 is adapted to communicate with the processing system 10 provided in the base station 1 via the communications networks 2, 4 to allow the above described process to be implemented. Accordingly, it will be appreciated that if the communications network 2 is the Internet, this will typically be achieved by having the base station 1 present web pages to the medical practitioner on the end station 3.

Accordingly, it will be appreciated that the end stations 3 may be formed from any suitable processing system, such as a suitably programmed PC, Internet terminal, lap-top, hand-held PC, or the like, which is typically operating applications software to enable data transfer and in some cases web-browsing.

In this case, the patient data, and any other information as well as input commands, may be supplied by the medical practitioner via the end station 3, before being transferred to the processing system 10, located at the base station 1. The processing system then operates as described above, transferring the results to the end station 3 for presentation to the medical practitioner.

In this case, it will be appreciated that access to the process may be controlled using a subscription system or the like, which requires the payment of a fee to access a web site hosting the process. This may be achieved using a password system or the like, as will be appreciated by persons skilled in the art.

Furthermore, information may be stored in the database 11, and this may be either the database 11 provided at the base station 1, the database 11 coupled to the LAN 4, or any other suitable database. This can also include patient data, results, determined parameters, or the like. This allows the medical practitioner to maintain a record of patient's medical condition history, which can be accessed as required at subsequent times. This may be used as an accurate record of the progression of the medical condition within the patient, and if coupled with a record of the medication actually provided to the patient, this can allow the effect of the medication to be determined.

It will be appreciated that by analysing data collected for a number of patients, this will allow more accurate models to be developed in an iterative process. Statistical analysis can also allow additional model to be developed, for example by analysing a range of age groups to create age dependent models.

EXAMPLE

A prophetic example of the technique as applied to a colony of cells in the human body is shown in Appendix A, below.

Variations

It will be appreciated from the above, that the techniques can be applied to any subject, and this includes, but is not limited to patients of human or other mammalian, or non-mammalian species and includes any individual it is desired to examine or treat using the methods of the invention. Suitable subjects that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

It will also be appreciated that the techniques can be used in vitro to examine the reaction of specific samples. Thus for example, the techniques can be used to monitor the reaction of cells to respective enviromnental conditions, such as combinations of nutrients or the like, and then modify the combination of nutrients, to thereby alter the cells response.

Furthermore, it will be understood that the terms "patient" and "medical condition" where used do not imply that symptoms are present, or that the techniques should be restricted to medical or biological conditions per se. Instead the techniques can be applied to any condition of the subject. Thus, for example, the techniques can be applied to performance subjects, such as athletes, to determine the subject's response to training. This allows a training program to be developed that will be able to prepare the subject for performance events, whilst avoiding overtraining and the like.

Thus, it will be appreciated that the condition of the subject may be the current physical condition, and particularly the readiness for race fitness, with the treatment program being a revised training program specifically directed to the athletes needs.

Thus, it will be appreciated that the techniques outlined above can provide:

(1) a method and apparatus for determining a medication program for a patient.

(2) a method and apparatus for determining a veterinary medication program for an animal suffering from a medical condition, and to a method and apparatus for determining livestock parameter values representing the effect of a medical condition on the subject animal;

(3) a method and apparatus for determining a non-linear control program for pharmaceutical, pharmacological or physiological processes, and to a method and apparatus for determining a process' parameter values representing the effect of some physical, biological or chemical intervention, influence or event on the process.

In the case of humans, the conditions to which the techniques are most ideally suited include conditions such as:

Parkinson's Disease
Schizophrenia
Bipolar disorders/manic depression
Cardiac disorders
Myasthenia gravis
Neuro muscular disorders
Treatment of cancerous and tumorous cells and related disorders
HIV/AIDS and other immune system disorders
Hepatic disorders
Athletic conditioning
Treatment of pathogens
Other disorders or diseases whose significant processes are capable of being reduced to a mathematical model An example of a mathematical model for Parkinson's disease is set out in Appendix B. In this regard, this is an example of a basic simple model, and is not intended to be limiting, but instead an example of the form of model that may be used.

However, it will be appreciated that the process can be implemented with respect to any condition for which it is possible to construct a mathematical model of the condition. This is not therefore restricted to medical conditions, although the techniques are ideally suited for the application to conditions, such as diseases or other medical disorders.

The initial construction of a mathematical model, and subsequent determination of subject data in the form of parameter values may be achieved using any suitable technique, examples of which include:

Model Reference Adaptive Control (MRAC);
Neural Networks;
Complex Systems analysis; and,
Kalman filters.

In this regard, the term Neural Networks will be understood to mean any method of creating mathematical models based on a supposed analogy with the functioning of the brain. In general, this is achieved by modelling the condition using a combination of non-linear functions including a suitably large number of terms to reduce mismatch errors. In this case, the model at a first approximation is a generic model that can be used to model almost any condition. This can then be trained through feedback, and associated restriction of parameters and the like, so that the model is constrained to model the respective condition of interest.

However, it will be appreciated that this is not intended to be limiting and any suitable technique could be used.

In any event, the system described above allows a mathematical model for the condition within a respective subject to be determined. Once this has been completed, the model is used to derive trajectories representing the progression of the condition under different circumstances, and in particular, under conditions of different medication or other treatment.

It will be appreciated that by calculating trajectories for the subject's current parameter and state variable values, this allows the progression of the condition within the subject to be determined. In this instance, if the subject is already receiving medication, this allows the potential success of the existing medication regime to be assessed, or in the case of an untreated subject, the progression of the condition if the subject remains untreated.

However, in addition to this, it is also possible to determine and assess a number of different trajectories for a range of different parameter and state variable values. This allows undesirable trajectories to be identified and eliminated, for example because they do not lead to a stable end point, or because they demonstrate chaotic behaviour, which would represent rapid fluctuations in the condition of the subject.

Once this has been completed, it is possible to define stability sets, which correspond to sets of parameter and state variable values for which the remaining solution trajectories are acceptable. Thus, this will correspond to trajectories that are non chaotic and result in the condition of the subject reaching a suitable end point, such as a stable or periodic region, within which the condition remains relatively unchanged.

Having determined the stability sets, it is then possible to determine the changes required to the subject's current parameter and state variable values in order to ensure that the progression of the condition within the subject ends up following one of the acceptable trajectories. Thus, this is achieved by determining a control program representing the effects of external influences on the subject's parameter and state variable values. The control program is developed by mathematically modelling the external factors, such as the effect of medication, and this can be achieved using one or more of:

Liapunov Functions;
Dynamic Optimisation algorithms (such as the Euler-Lagrange Method);
a Convex Set Algorithms (such as Kuhn-Tucker);
Any other suitable algorithm.

The control program therefore represents a treatment program, such as a medication regime, which will cause the subject's parameter and state variable values to be modified towards those in the stability sets.

This therefore allows medication or the like to be prescribed on a case by case basis, to thereby ensure that subjects receive medication according to tailored regimes, thereby helping the subject progress to a condition state defined by one of the stability sets.

It will be appreciated that this will ideally lead to a stable end point or region representing the elimination of the condition. However, this is not always possible, and instead it may be necessary to select trajectories that head to a stable end point or region within which the symptoms and/or effects of the condition are either minimised, contained, or stabilised.

Persons skilled in the art will appreciate that numerous variations and modifications will become apparent. All such variations and modifications which become apparent to persons skilled in the art, should be considered to fall within the spirit and scope that the invention broadly appearing before described.

APENDIX A

1 Problem Statement:

Consider an isolated contiguous colony of cells in the human body, of population $x(t)$ cells for $t \geq 0$. This colony goes through successive generations of cells, whereby given sufficient resources, the rate of increase is proportionate to the existing population. However, there is competition for the finite resources (oxygen, blood etc.) provided by the colony's environment, and so rate of increase is increasingly retarded as the population expands. For a sufficiently large population, the rate of growth becomes negative, as cells die from inadequate nourishment.

This colony of cells secretes a substance S that is important for the well-being of the patient. Secreted by the colony into its external environment at a molar concentration y(t), this substance is eventually taken up by nearby protein transport mechanisms and used elsewhere. Rate of secretion takes the form of Michaelis-Menten kinetics, with the rate saturating to a maximum once the colony's population becomes sufficiently large. Thus we can write a simple formulation of this system's dynamics as being $$\dot{x} = x(t)(P - Rx(t)) \int (x(t)) \quad (1)$$

$$\dot{y} = \frac{K_1 x(t)}{K_2 + x(t)} \int (x(t)) - \mu y(t) \int (y(t)) \quad (2)$$

where P is the uninhibited population growth coefficient, R is the population retardation coefficient due to finite resources, $K_1$ and $K_2$ represent Michaelis-Menten quantities (more usually denoted $V_M$ and $K_M$), $\mu$ is rate of uptake of S by transport mechanisms, and $\int (z)$ denotes the one-sided Heaviside function. Equation (1) is a more complicated form of the famous "logistic equation".

2 Medical Problem:

A pathology is observed among a small percentage of the population, whereby y(t) fluctuates sharply without apparent physical cause. In the medical community this condition is known as "Y's Disease". In case studies, it is observed that in some sufferers such fluctuations become progressively worse over a timespan of months or years, totally incapacitating the patient, until they become completely erratic, leading to death.

The three forms of medication at our disposal are a hormone (denoted $u_1$) to stimulate the rate of unconstrained growth P of the cellular population;

a hormone (denoted $u_2$) that strongly suppresses the rate of unconstrained growth P of the cellular population (not conventionally used in treating Y's Disease); and conventional medications to inhibit (denoted $u_3$) or stimulate (denoted $u_4$) the rate of uptake is of y(t).

Treatments involving these medications have not been particularly effective. Clinical trials using the growth hormone $u_1$ have, in some patients, unexpectedly led to death, while control of $\mu$ has often been of fluctuating usefulness.

3 Parameter Identification, in Vivo and in Vitro:

These dynamics are happening within a living patient. With present technology, $P_i$ R, $K_2$ and x(t) cannot be measured in vivo directly in any meaningful way; $K_1$ can be estimated in vitro. y(t) can be measured non-invasively using fMRI, to a tolerance of $\pm \delta y$.

Instead of using conventional statistical methods of parameter estimation, which are virtually useless under the circumstances, we construct model equations and a dynamic identifier algorithm (process illustrated in FIG. 3A). Given a sufficiently large time-series of measurements $\{y(t_1), (t_2), \ldots, y(t_n)\}$, we are able to estimate the parameter values for our specific patient to within an accuracy partly governed by the length of this dataset, as the model coefficients converge to those of the system. If no such convergence takes place, then this may indicate a structural disparity between modelling assumptions and the physical system Different forms of model equations can be employed and cross-correlated (e.g. $\dot{x} \sim x(t) (P-R x^2(t)) \int (x(t))$, to confirm we have the best match of model to patient. Sufferers of the same medical condition, at the same stage of the condition, should have models with a common structure, although the actual parameter values may vary from patient to patient.

Having obtained these parameter estimates, they are substituted into the model equations to simulate the system. This is to check for validity, by generating output from the model and correlating this with the original patient output.

This identification process is repeated on a sufficiently large population of human or animal analogues to quantify the effects of the available medications (listed above) on the system. As a consequence, it is found that the medicated system can be written $$\dot{x} = x(t)((P + u_1 - u_2) - Rx(t)) \int (x(t)) \quad (3)$$

$$\dot{y} \frac{K_1 x(t)}{K_2 + x(t)} \int (x(t)) - (\mu + u_3 - u_4) y(t) \int (y(t)) \quad (4)$$

where $$u_1 \in [0, 0.15] \quad (5)$$

$$u_2 \in \{[-1, -0.5], 0\} \quad (6)$$

$$u_3 \in [0, 0.2] \quad (7)$$

$$u_4 \in [0, 0.1]. \quad (8)$$

These constraints are imposed by drug safety concerns, or, in the case of $u_2$, the lack of fine control in delivering the hormone to the location.

Equations (3), (4) constitute the state equations of the system, more formally written $$\dot{z} = f(z, u, \lambda, t) \quad (9)$$

where $z=[x(t), y(t)]^T$, $u=[u_1(t), u_2(t), u_3(t), u_4(t)]^T$ and $\lambda=[P, R, K_1, K_2, \mu]^T$.

For our specific patient, we find the reference model of the identifier algorithm converges asymptotically to ODEs of the form of equations (1), (2), with normalized parameter values R=1.6; P=2; $K_1$=10; $K_2$=0.8 and $\mu$=1.2 when the patient is unmedicated, i.e. u=0.

4 Global Stability Analysis

Figure 3B:
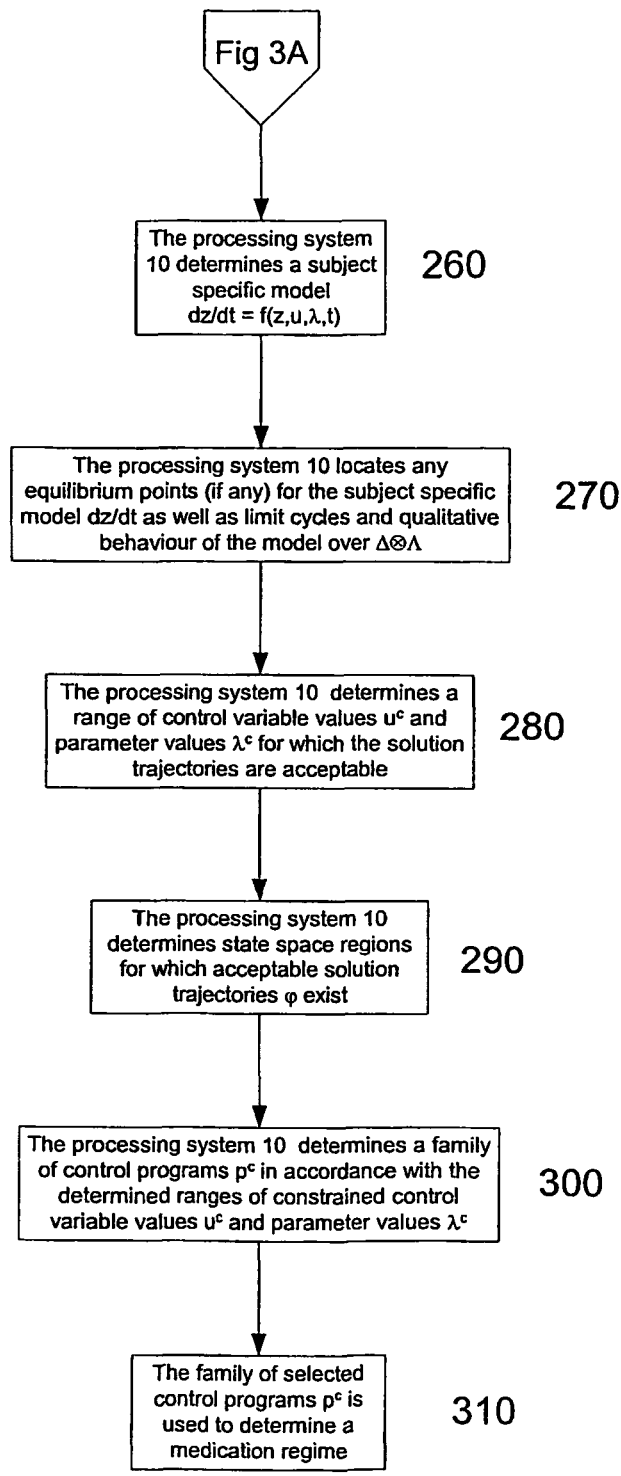
Figure 11:
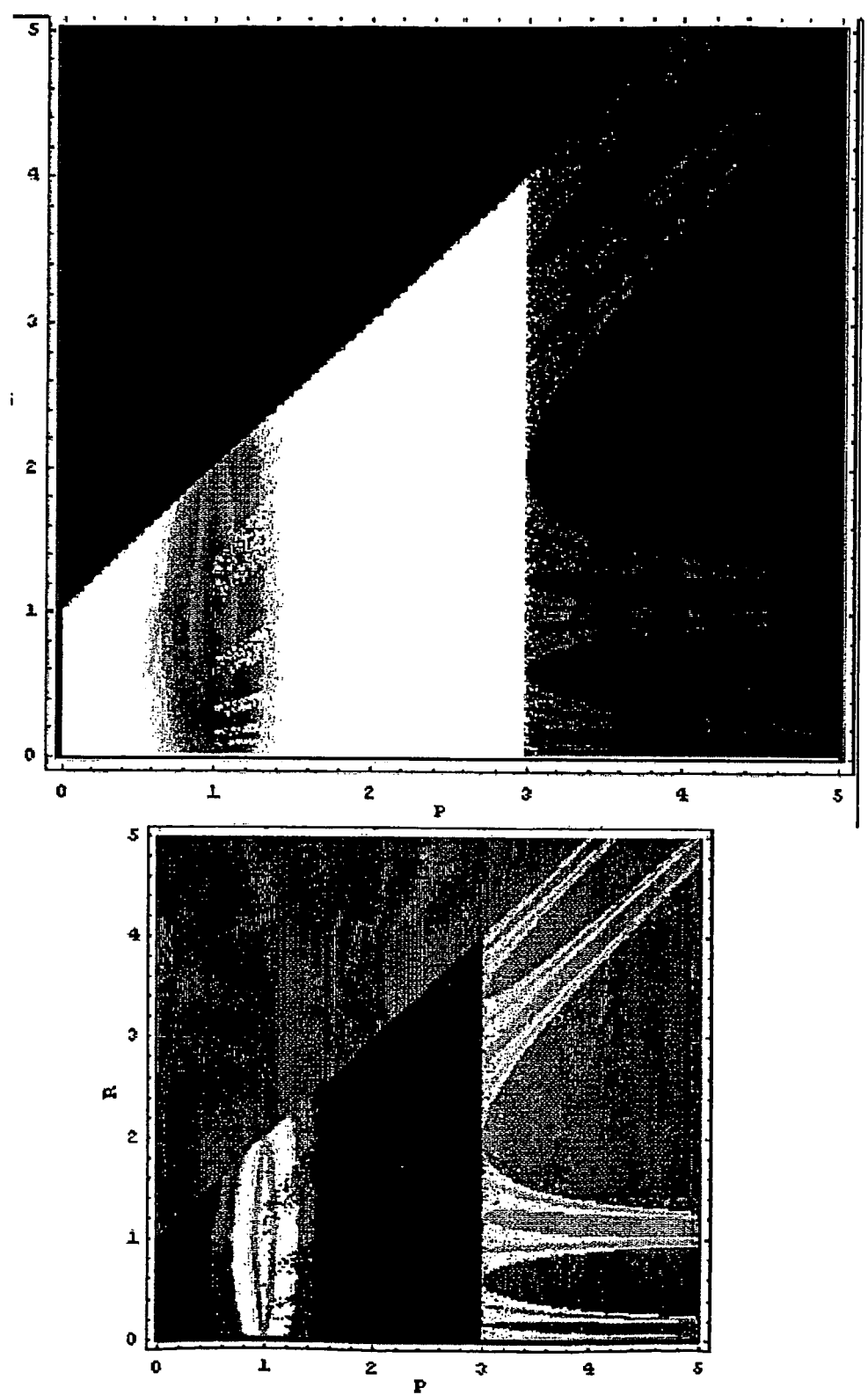
FIG. 11 is an example of a convergence map for a range of values of P against R, for the prophetic example outlined in Appendix A.

As illustrated in FIG. 3B, a global stability analysis is conducted on the structure of equations (1) and (2), across a range of values for P and R (FIG. 11). The top illustration of FIG. 11 is a convergence map, of repeated iterations on x(0)=1. Dark grey denotes stability (the sequence converges eventually); black denotes extreme stability (the sequence tends immediately to a final value, usually extinction) and white denotes no final convergence after a designated number of iterations—in this case, five thousand—either due to the sequence diverging, or else the onset of chaos. The bottom illustration is a false colour contrast enhancement of this convergence map, rendered here in B&W.

Figure 12:
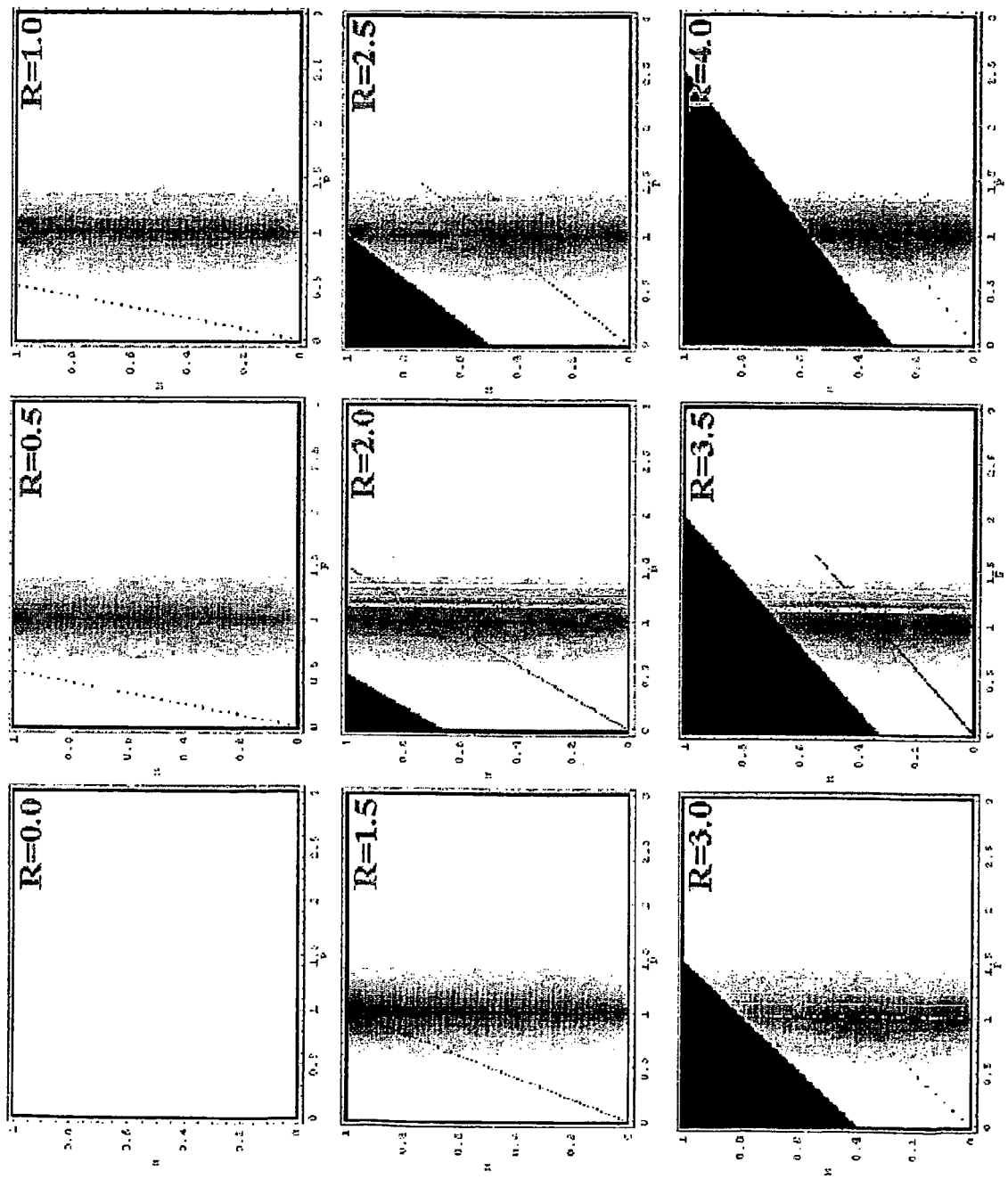
FIG. 12 is an example of a second set of convergence maps for a range of values of x(0) against P for fixed values of R, for the prophetic example outlined in Appendix A.

To measure the dependence (if any) of these maps on our initial choice of x(0), a second, "chequer board" set of convergence maps is generated, of x(0) against P for fixed values of R. This is depicted in FIG. 12.

It can be seen from the structure of FIG. 11 that

1. This system is susceptible both to chaos and to extinction;

2. That, consequently, the manifestation of strong fluctuations in y(t) in "Y's Disease" need not necessarily be a disease at all, but a peturbation of the dynamics of an otherwise healthy system into a region of instability or extinction;

3. That, therefore the unexpected deaths of patients under $u_1$ growth-hormone therapy need not imply any inherent toxicity of the hormone, but be due to the inducing of chaos or even the extinction of the system evident for $P+u_1$ being pushed to too high a value (e.g. $P+u_1 \geq 3$);

4. That, given the complex population dynamics of the underlying cell colony, attempts to control y(t) without controlling x(t) are futile; hence, modification of the cell population using hormones $u_1$, $u_2$ is fundamental to medicating the patient. Contrary to expectation, conventional medications $u_3$ and $u_4$ that alter uptake of y(t) can only ever be of limited practical use in regulating y(t);

5. The most stable region of this system is in neighbourhoods surrounding $\{P=1, R<<2\}$, although even here there exist dangerous zones of chaotic structure (marked white in upper illustration and black in lower, FIG. 11).

For specified values of P and R, there exists two pairs of equilibrium points $[x^*, y^*]^T$ such that $$\dot{x}(x^*, y^*) = \dot{y}(x^*, y^*) \equiv 0, \tag{10}$$

namely, $$[x_1^*, y_1^*]^T = (0, 0), \tag{11}$$

and $$[x_2^*, y_2^*]^T = \left(\frac{P}{R}, \frac{K_1 P}{\mu(K_2 R + P)}\right). \tag{12}$$

The first of these points corresponds with the trivial equilibrium of extinction; the second, of a dynamic non-zero equilibrium of the population (visible in the frames of FIG. 12 as a line of black dots).

5 Single-Liapunov Control

Figure 13:
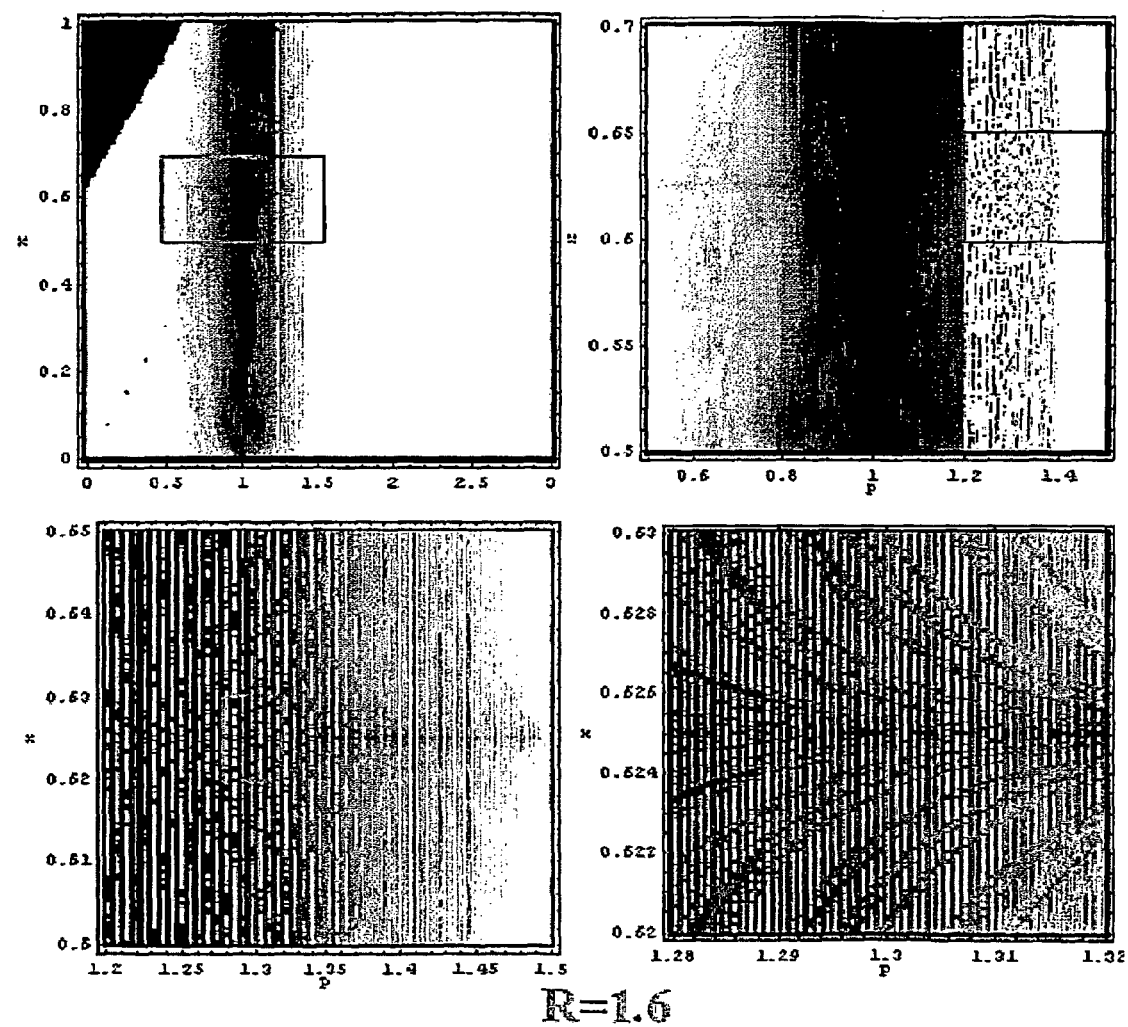
FIG. 13 is an example of a number of levels of magnification for a selected one of the convergence maps of FIG. 12.

The next task is to control the system, steering it into a stable configuration to improve the patient's condition (the process depicted in FIGS. 4A and 4B). An early step of this is to decide upon a desired target set $\tau_1$. As illustrated at various levels of magnification in FIG. 13, this partly depends upon the scale of the system. As well as the large-scale pool of stability visible for $P \in [0.8, 1.19]$, even within the chaotic domain $P \in [1.2, 1.4]$ small locally-stable neighbourhoods appear to exist.

Figure 14:
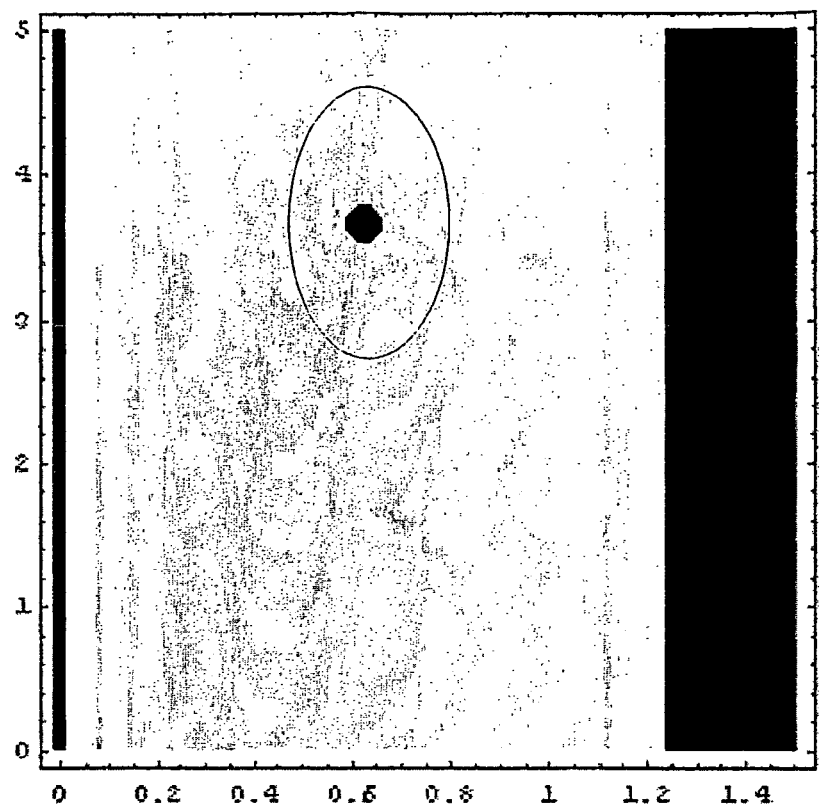
FIG. 14 is an example of a set of target points for the prophetic example outlined in Appendix A, shown in greyscale and false colour; and, FIG. 15A is an example of candidate solution trajectories for the prophetic example outlined in Appendix A.
Figure 14:
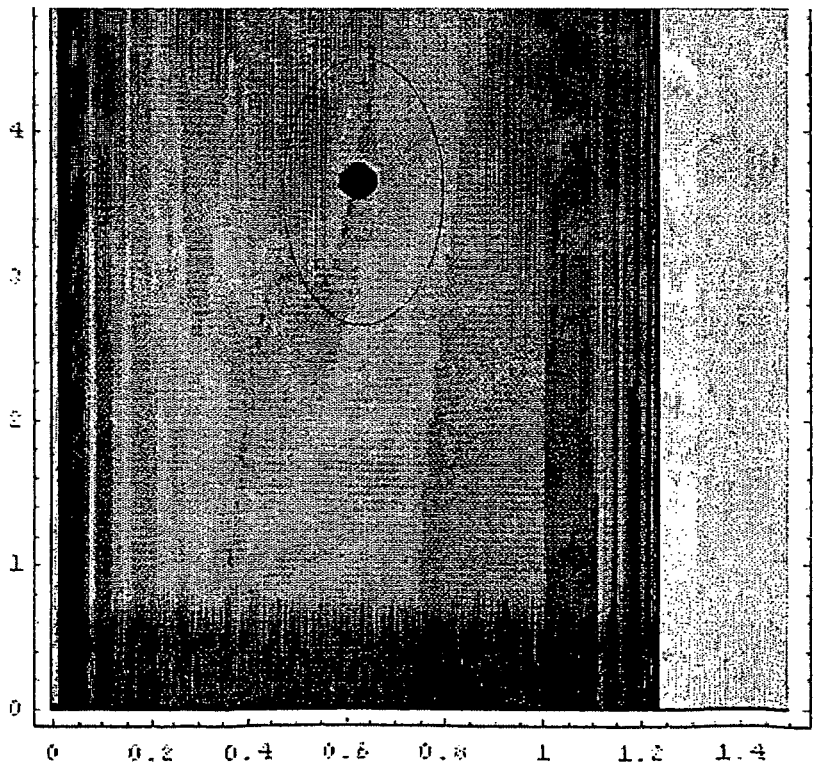

In the case of this patient, the cell colony is to have its growth parameter permanently translated to $P \mapsto I$, by setting $u_2(t) \equiv -1 \; \forall t$. In the XY plane for $P=1$, $R=1.6$, we then define $\tau_1$ to be a neighbourhood of the stable equilibrium point $[x^*_2, y^*_2]^T$. This is illustrated in FIG. 14, where the relative stability of points $[x(t), y(t)]^T$ is mapped left in the usual grey-scale (black=extreme convergence, white=failure to converge) and eight using false-colour shading to enhance differences in relative stability, rendered here in B&W. The equilibrium point $[x^*_2, y^*_2]^T$ is tagged by a dark point, and can be seen to lie on a thin curve of relatively stable points. The elliptical neighbourhood that constitutes $\tau_1$ is shown. All points that reach this neighbourhood will converge to $[x^*_2, y^*_2]^T$.

Figure 15A:
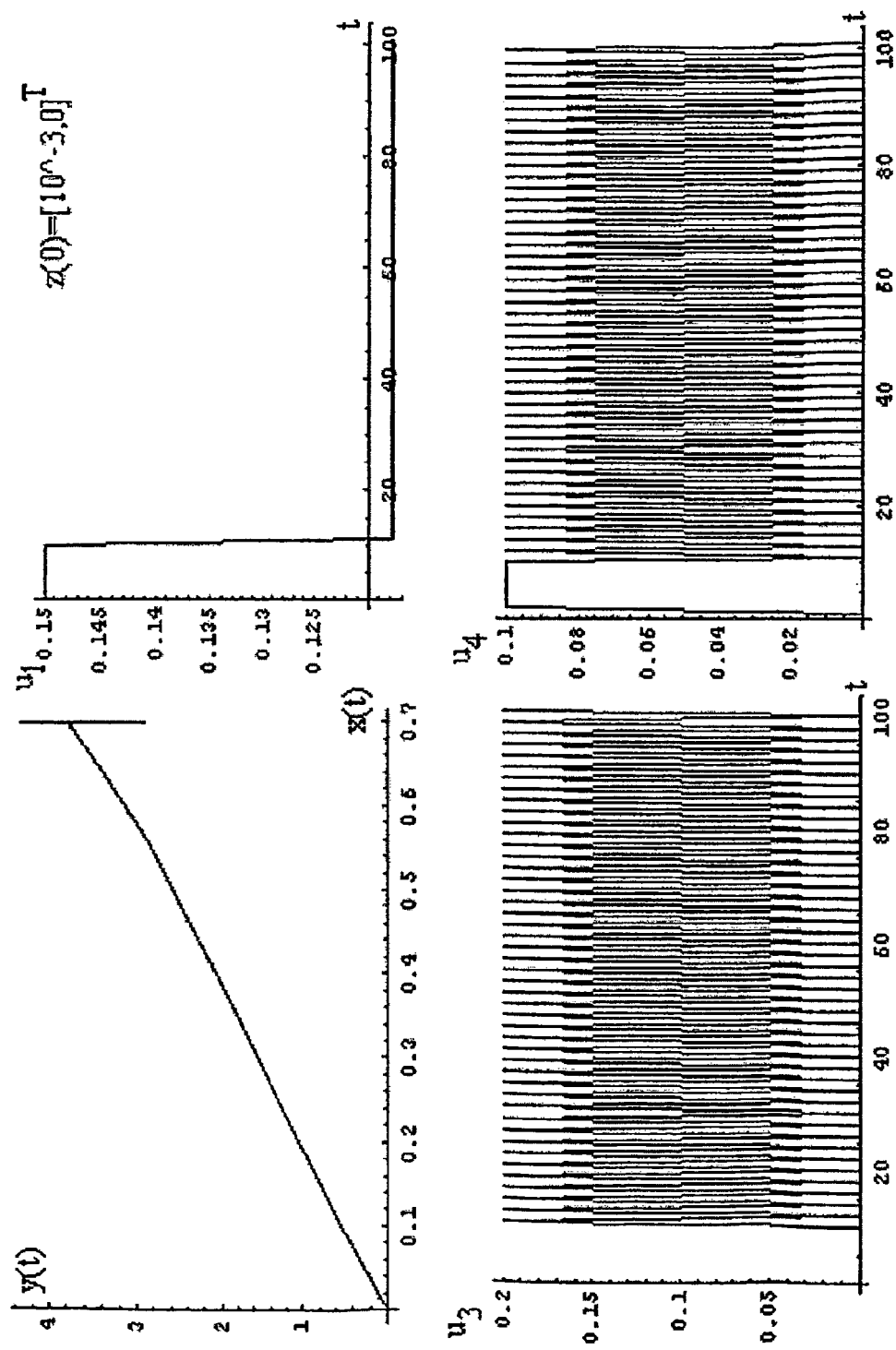
FIG. 15B is an example of alternative solution trajectories for the prophetic example outlined in Appendix A; and, FIG. 16 is an example of candidate solution trajectories for the prophetic example outlined in Appendix A using a double Liapunov function.
Figure 15B:
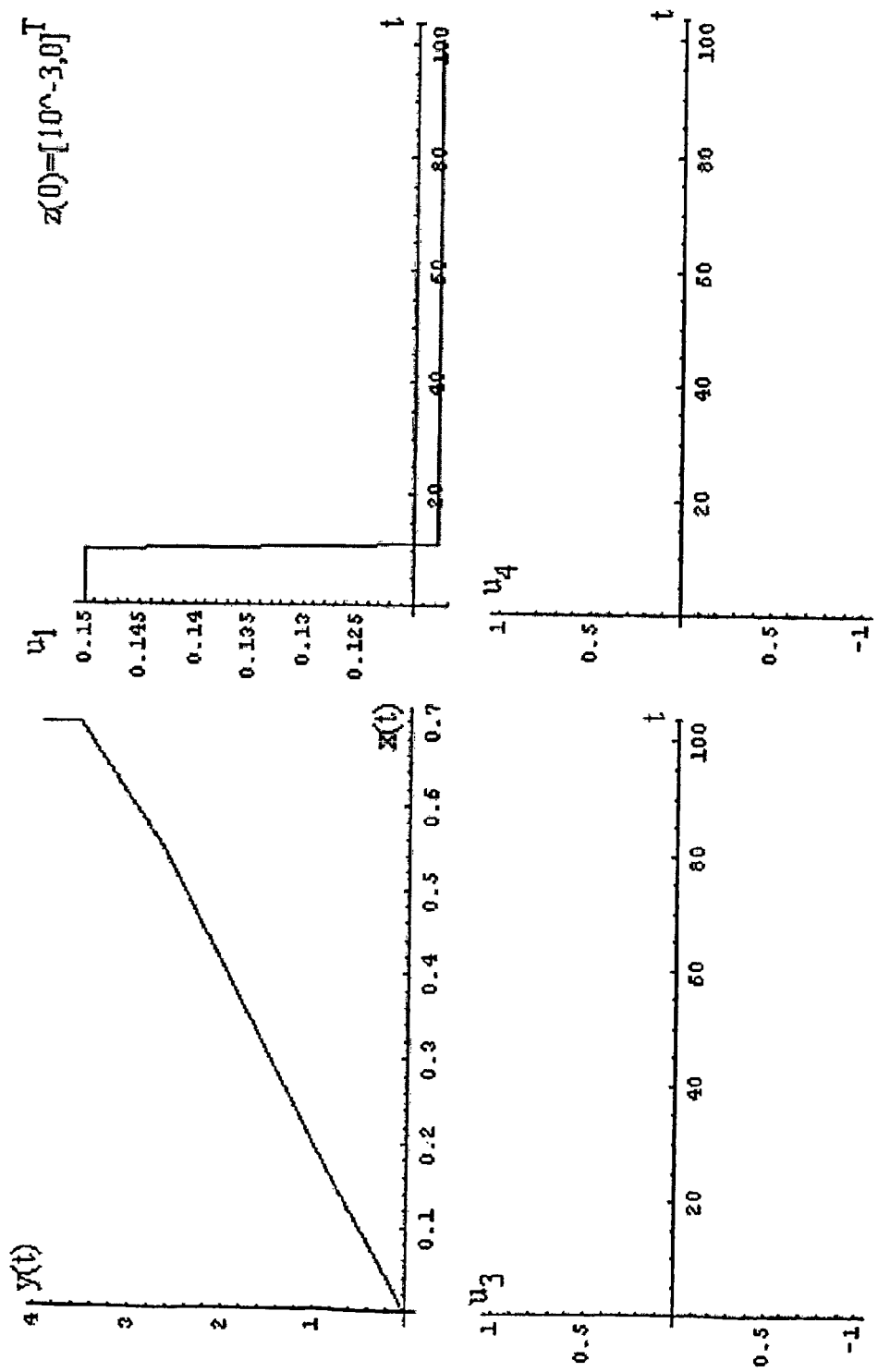

A Liapunov function $V_1$ is then constructed around the geometry of $\tau_1$, and a control program p* computed using $\nabla V_1 \cdot f(z, u, \lambda, t) \leq 0$, to use the constrained $u_1$, $u_3$ and $u_4$ to steer the patient's state to $\tau_1$. Candidate solution trajectories are computed and presented to the clinician (e.g. see FIG. 15a, for a solution trajectory issuing from the point $[x(0), y(0)]^T = [0.001, 0]^T$). If these solution trajectories or p* are in some sense unsatisfactory, quantitative optimization is performed (e.g. FIG. 15b shows a slightly different trajectory steered from the same initial conditions to the target set, in which some robustness is sacrificed in order to abandon any reliance upon the medications $u_3$, $u_4$).

The set of all z(0) from which such $V_1$-derived control is possible is computed and denoted $R^q$.

6 Double-Liapunov Control

Now consider the problem where there exists uncertainty about the precise value for R. This may be due to background fluctuations preventing the identification algorithm from attaining a more precise estimate of R than $R \pm \delta R$, or it may be that the patient's biology engages in a potentially adverse response when P is modified via hormone therapy, whereby R actually is shifted by amount $\delta R$. Perhaps this is due to the disease, or possibly it is a natural body mechanism* Either way, it is necessary to repeat the control process of the previous section in such a way that it is guaranteed to be robust against such fluctuations (the process depicted in FIGS. 6, 7a and 7b).

The equations (3), (4) are re-written, $$\dot{x} = x(t)((P + u_1 - u_2) - (R + w)x(t)) \int (x(t)) \tag{13}$$

$$\dot{y} \frac{K_1 x(t)}{K_2 + x(t)} \int (x(t)) - (\mu + u_3 - u_4)y(t) \int (y(t)) \tag{14}$$

where $w \in [-w^+, w^+]$ and $w^+$ denotes the maximum possible fluctuation in R, estimated for our human patient to be $w^+ = 0.1$.

In this "Game against Nature" it is assumed that these fluctuations are deployed intelligently and aggressively against our control strategies by a player designated "Nature", in an attempt to disrupt the system. The task is then to design control strategies that are robust against any such interference. The target set $\tau_{1w}$ and Liapunov function $V_{1w}$ are taken to be the same as $\tau_1$, $V_1$. To decide upon appropriate choices for $\tau_2$, FIG. 11 and FIG. 12 are re-examined. Even at $R \mapsto 1.1$, it is clear that for $P=1$, domains corresponding to extinction cannot easily be reached by Nature directly; the most immediate way to disrupt population dynamics is by driving x(t) either to $x(t) \to 0$ or $x(t) \to x >> 1.2$. A value of $x' = 1.4$ is chosen, and a neighbourhood around this nominated as $\tau_2$.

Figure 16:
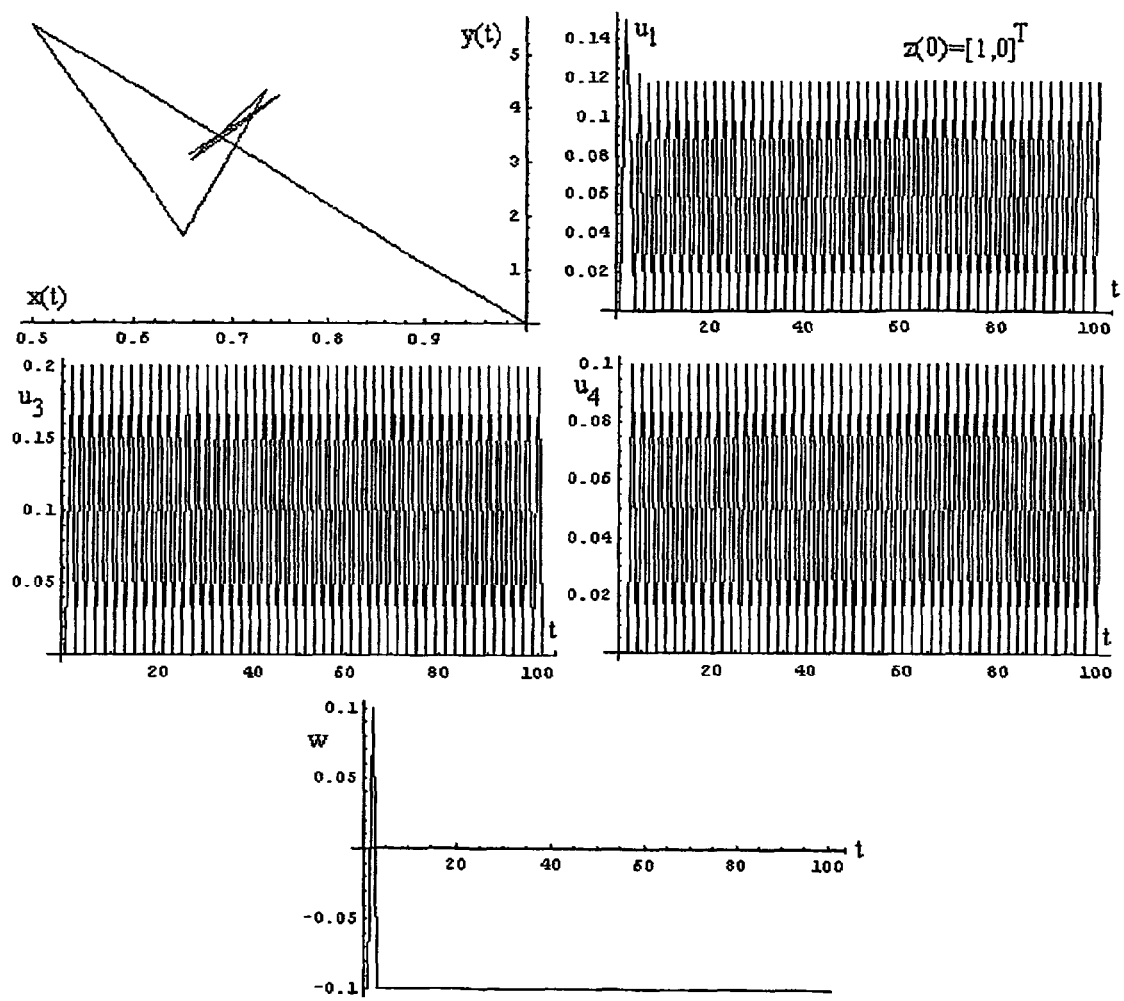

An appropriate Liapunov function $V_2$ is designed, and Nature strategies p generated such that $\nabla V_2 \cdot f \leq 0$ and p attempts to obstruct our control efforts. The control strategy p*$^w$ is computed, based on the criterion $\nabla V_{1w} \cdot f \leq 0$. The sets $W_1$ (points $[x(0), y(0)]^T$ from which p*$^w$ steers trajectories safely into $\tau_{1w}$, against all possible w) and $W_2$ (points $[x(0), y(0)]^T$ from which p** steers trajectories into $\tau_2$ despite all possible u) are plotted. As before, given $[x(0), y(0)]^T$, candidate solution trajectories are computed under p*$^w$ and presented to the clinician (e.g. see FIG. 16, for a solution trajectory issuing from the point $[x(0), y(0)]^T = [1, 0]^T$, giving successful control programs for u despite the counterattack w). These control programs can be subjected to another layer of optimization, or else the constraints $[u^-, u^+]$, $[w^-, w^+]$ modified to improve clinical control of the patient.

Thus it has been demonstrated that these tools can be employed to transform the medication of patients through (a) dynamic parameter, and state estimation, (b) the calculation of single function control and (c) the computation of robust control in the presence of random or actively hostile elements. In most cases such medication control strategies will be profoundly different from those of conventional empirical medication.

APPENDIX B

The equations set out below represent a simple 3-equation model of exogenous dopamine pharmacokinetics in the synaptic cleft of a dopaminergic neuron.

$$\frac{d[l_e]_{bb}}{dt} = A \sin(wt + \phi) - \frac{k_{11}^{bb}[l_e]_{bb}}{k_{12}^{bb} + [l_e]_{bb}} - \mu_{bb}[l_e]_{bb};$$

$$\frac{d[l_e]_{syn}}{dt} = \frac{k_{11}^{bb}[l_e]_{bb}}{k_{12}^{bb} + [l_e]_{bb}} - \frac{k_{11}^{dopa}[l_e]_{syn}}{k_{12}^{dopa} + [l_e]_{syn}} - \mu_{lsyn}[l_e]_{syn};$$

$$\frac{d[d_e]_{syn}}{dt} = \frac{k_{11}^{dopa}[l_e]_{syn}}{k_{12}^{dopa} + [l_e]_{syn}} - \frac{k_{11}^{dat}[d_e]_{syn}}{k_{12}^{dat} + [d_e]_{syn}} - \mu_{syn}[d_e]_{syn} + \langle d_o \rangle;$$

where:

$[l_e]_{bb}$: levodopa concentration in bloodstream
$k_{11}^{bb}$, $k_{12}^{bb}$: levodopa transport parameters across blood-brain barrier
$\mu_{bb}$: "sink" coefficient for levodopa in bloodstream
$[l_e]_{syn}$: levodopa concentration in synaptic cleft
$k_{11}^{dopa}$, $k_{12}^{dopa}$: conversion parameters for dopa decarboxylase
$\mu_{lsyn}$: "sink" coefficient for levodopa in cleft
$[d_e]_{syn}$: dopamine concentrarion in synaptic cleft
$k_{11}^{dat}$, $k_{12}^{dat}$: dopamine transport coefficients for neuron mass
$\mu_{dsyn}$: "sink" coefficient for dopamine in cleft
$\langle d_o \rangle$: mean concentration of signalling dopamine
A, w, $\phi$: control variables for introducing levodopa into blood Accordingly, it will be appreciated by persons skilled in the art that the above mentioned equations can be used in determining a model representing the progression of Parkinson's disease within a subject.

The invention claimed is:

1. A method of determining a treatment program for a subject, the method being performed by a processing system, the method comprising:
   a) obtaining subject data, the subject data representing the subject's a condition of the subject;
   b) constructing a mathematical model comprising one or more differential equations representing a progression of the condition, the progression being a development of the condition over time;
   c) analyzing, using the processing system, the subject data and the model of the condition to determine system values representing the condition;
   d) determining, using the processing system, one or more solution trajectories, the solution trajectories being solutions to the differential equations and representing potential routes of progression of the condition within the subject, the solution trajectories being determined in accordance with the model and the determined system values; and
   e) determining a treatment program in accordance with the determined solution trajectories.

2. A method according to claim 1, the subject data representing a medical condition for the respective subject, the method comprising determining solution trajectories representing the progression of the medical condition within the subject.

3. A method according to claim 1, each system value representing a quantity obtained for the measurement of a respective attribute of the condition, the system values comprising:
   a) state variable values representing rapidly changing attributes; and
   b) parameter values representing slowly changing or constant attributes.

4. A method according to claim 1, the method comprising determining control variable values, the control variables representing attributes of the condition that can be externally controlled.

5. A method according to claim 4, the model comprising one or more model equations representing the condition, the method comprising determining one or more subject equations in accordance with the model equation(s) and the system values.

6. A method according to claim 5, the method of determining the treatment program comprising:
   a) evaluating the behavior of solution trajectories representing solutions of the subject equations;
   b) determining a set of target points, the target points comprising stable points for the subject equation(s); and
   c) determining one or more control programs, each control program comprising a sequence of control variable values that result in solution trajectories having desired behavior comprising at least one of:
      i) the solution trajectories are acceptable based on predefined criteria;
      ii) the solution trajectories do not move away from the target points; and
      iii) the solution trajectories finally approach the target points.

7. A method according to claim 6, the method comprising determining the solution trajectories to be acceptable if the solution trajectories are- non-chaotic; and sufficiently smooth so that the solution trajectories represent progressions of the condition that do not adversely affect the subject.

8. A method according to claim 6, the method of evaluating the behavior of the solution trajectories comprising:
   a) determining regions of control variable and/or parameter values for which the solution trajectories are chaotic; and
   b) determining ranges of the control variable and/or parameter values for which the solution trajectories can be made non-chaotic, or otherwise stabilized.

9. A method according to claim 8, the method comprising determining one or more control programs in accordance with the determined ranges.

10. A method according to claim 8, the method comprising using a Liapunov function to determine the one or more control programs.

11. A method according to claim 10, the method comprising:
   a) defining a Liapunov function for which the gradient defines solution trajectories moving towards the target points;
   b) defining constraints on the control variable values; and
   c) determining control variable values that result in solution trajectories travelling down the gradient of the Liapunov function in accordance with the constraints.

12. A method according to claim 11, wherein the constraints comprise limits on the treatment that can be provided to the subject.

13. A method according to claim 8, the method comprising determining a treatment in accordance with one or more of the determined control programs by:
   a) viewing a representation of the solution trajectories, the representation comprising an indication of the chaotic regions; and
   b) selecting a control program in accordance with the represented solution trajectories.

14. A method according to claim 6, the method comprising:
   a) determining one or more Nature values, the Nature values being quantities of Nature parameters and/or variables representing attributes of the condition that will cause the condition to progress in an undesirable manner;
   b) modifying the subject equations to incorporate the one or more Nature values;
   c) evaluating the behavior of modified solution trajectories representing solutions of the modified subject equations; and
   d) performing at least one of:
   i) determining one or more control programs, each control program comprising control variable values that result in modified solution trajectories having desired behavior; and
   ii) determining a set of undesired points, the undesired points comprising unstable points for the subject equation(s); and
   iii) determining one or more undesired programs, each undesired program comprising Nature values that result in modified solution trajectories having undesired behavior comprising at least one of:
   (1) the modified solution trajectories are unacceptable based on predefined criteria;
   (2) the modified solution trajectories do not move away from the undesired points; and
   (3) the modified solution trajectories finally approach the undesired points.

15. A method according to claim 14, the method comprising, using the modified solution trajectories, the method of evaluating the behavior of the solution trajectories comprising:
   a) determining regions of control variable and/or parameter values for which the solution trajectories are chaotic; and
   b) determining ranges of the control variable and/or parameter values for which the solution trajectories can be made non-chaotic, or otherwise stabilized.

16. A method according to claim 15, the method comprising:
   a) defining a second Liapunov function for which the gradient defines modified solution trajectories moving towards the undesired points;
   b) defining constraints on the Nature values; and
   c) determining Nature values that result in modified solution trajectories travelling down the gradient of the second Liapunov function in accordance with the constraints.

17. A method according to claim 16, the method comprising determining the treatment program in accordance with control programs and the Nature programs by:
   a) determining starting points having modified solution trajectories for which control programs exist;
   b) determining starting points having modified solution trajectories for which Nature programs exist;
   c) viewing a representation comprising at least one of: i) the modified solution trajectories; ii) the starting points; and iii) the chaotic regions; and
   d) selecting a control program in accordance with one or more represented solution trajectories.

18. A method according to claim 2, the method comprising determining parameter values by:
   a) determining a partial set of system values from the subject data;
   b) selecting one or more models, each model comprising one or more equations representing the effect of a condition on a subject;
   c) determining a complete set of system values in accordance with the determined partial set of system values and the respective equations; and
   d) selecting a model in accordance with the determined complete set of system values.

19. A method according to claim 18, the step of determining the complete set of system values comprising:
   a) determining a candidate set of system values in accordance with the determined partial set of system values and the equations;
   b) comparing the candidate set of system values to at least one of: i) the partial set of system values; and ii) predetermined thresholds; and
   c) selecting the model in accordance with the result of the comparison.

20. A method according to claim 1, the method comprising: a) determining stability sets; and b) determining the treatment in accordance with the stability sets.

21. A method according to claim 20, wherein the stability sets represent combinations of state and parameter values for which the resulting solution trajectories are acceptable.

22. A method according to claim 20, the method comprising determining a control program in accordance with the stability sets.

23. A method according to claim 21, the method comprising: a) considering subject state variable and parameters values for the subject;
   b) determining modification of the state variable and parameter values required such that the subject's state variable and parameter values fall within the stability sets; and
   c) determining the treatment program in accordance with the required modification of the state variable and parameter values.

24. A method according to claim 19, the method comprising determining a medication dosage regime in accordance with the determined stability sets.

25. A method according to claim 1, the method comprising determining a control program using one or more of: a) Liapunov functions; b) dynamic optimization techniques; c) convex set algorithms.

26. A method according to claim 1, wherein the subject is a patient.

27. A method according to claim 1, wherein the treatment is the administration of medication.

28. Apparatus for determining a treatment program for a subject, the apparatus comprising a processing system adapted to:
   a) obtain subject data, the subject data representing a condition of the subject;
   b) constructing a mathematical model is constructed comprising one or more differential equations representing a progression of the condition, the progression being a development of the condition over time;
   c) analyze the subject data and the model of the condition to determine system values representing the condition;
   d) determine one or more solution trajectories, the solution trajectories being solutions to the differential equations and representing potential routes of progression of the condition within the subject, the solution trajectories being determined in accordance with the model and the determined system values; and e) determine a treatment program in accordance with the determined solution trajectories.

29. A method according to claim 1, wherein the step of analyzing the subject data comprises:

a) determining a partial set of system values from the subject data, each system value representing a quantity obtained by the measurement of a respective attribute of the condition;

b) determining a plurality of models, each model comprising one or more equations representing the effect of a condition on a subject;

c) calculating a complete set of system values in accordance with the partial set of system values and the respective equation, for each model; and d) selecting one model of the plurality of models in accordance with the determined complete set of system values.

30. A method according to claim 29, wherein the system values comprise:

a) state variable values representing rapidly changing attributes; and b) parameter values representing slowly changing or constant attributes.

31. A method of claim 29, wherein calculating the complete set of system values comprises:

a) determining a candidate set of system values in accordance with the determined partial set of system values and the equations;

b) comparing the candidate set of system values to at least one of the partial set of system values, and predetermined thresholds; and c) selecting the model in accordance with the result of the comparison.

32. A method according to claim 1, further comprising the step of determining the effectiveness of treatment provided to a subject, the effectiveness determination comprising:

a) repeating the steps of obtaining subject data and analyzing the subject data to determine modified system values;

b) comparing the system values and the modified system values; and c) determining the effect of the treatment in accordance with the results of the comparison.

* * * * *